(12) United States Patent
Reuel et al.

(10) Patent No.: US 10,890,582 B2
(45) Date of Patent: *Jan. 12, 2021

(54) SENSOR FOR DETECTING ANALYTES

(71) Applicant: Massachusetts Institute of Technology, Cambridge, MA (US)

(72) Inventors: Nigel F. Reuel, Cambridge, MA (US); Michael S. Strano, Lexington, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/185,856

(22) Filed: Feb. 20, 2014

(65) Prior Publication Data

US 2014/0234856 A1 Aug. 21, 2014

Related U.S. Application Data

(60) Provisional application No. 61/767,516, filed on Feb. 21, 2013.

(51) Int. Cl.
| | | |
|---|---|---|
| *G01N 33/58* | (2006.01) | |
| *B82Y 30/00* | (2011.01) | |
| *G01N 33/543* | (2006.01) | |

(52) U.S. Cl.
CPC ....... *G01N 33/5436* (2013.01); *G01N 33/587* (2013.01); *G01N 2458/30* (2013.01)

(58) Field of Classification Search
CPC ...... G01N 21/76; G01N 33/58; A61B 5/1459; B82Y 30/00
See application file for complete search history.

(56) References Cited

U.S. PATENT DOCUMENTS

| | | | |
|---|---|---|---|
| 5,114,676 A | 5/1992 | Leiner et al. | |
| 8,377,700 B2* | 2/2013 | Strano et al. | 436/86 |
| 8,765,488 B2* | 7/2014 | Strano et al. | 436/529 |
| 9,901,295 B2* | 2/2018 | Iverson | B82Y 30/00 |
| 9,980,668 B2* | 5/2018 | Strano | A61B 5/1459 |
| 2007/0292896 A1* | 12/2007 | Strano et al. | 435/7.9 |
| 2010/0279421 A1* | 11/2010 | Strano et al. | 436/86 |
| 2011/0212463 A1 | 9/2011 | Delouise | |
| 2013/0035567 A1* | 2/2013 | Strano | A61B 5/14532 600/316 |
| 2015/0133752 A1* | 5/2015 | Iverson | B82Y 30/00 600/316 |

OTHER PUBLICATIONS

Kozolvskaya et al., "Ultrathin Layer-by-layer Hydrogels with Incorporated Gold Nanorods as pH-Sensitive Optical Materials," published Oct. 23, 2008.*
Yu et al., "Chitosan-Grafted Multi-Walled Carbon Nanotubes for Sustained Releasing of Pazuflozacin Mesilate," published 2010.*
(Continued)

*Primary Examiner* — Tracy Vivlemore
*Assistant Examiner* — Nam P Nguyen
(74) *Attorney, Agent, or Firm* — Honigman LLP

(57) ABSTRACT

A sensor for detecting an analyte can include a photoluminescent nanostructure embedded in a sensor hydrogel. The sensor hydrogel can be supported by a substrate hydrogel.

20 Claims, 28 Drawing Sheets

(56) References Cited

OTHER PUBLICATIONS

Reuel et al., "Transduction of Glycan-Lectin Binding Using Near-Infrared Fluorescent Single-Walled Carbon Nanotubes for Glycan Profiling," J. Am. Chem. Soc., vol. 133, 17923-17933, published Oct. 4, 2011.*
Wang et al., "Label-free hybridization detection of a single nucleotide mismatch by immobilization of molecular beacons on an agarose film", Nucleic Acids Research, vol. 30, No. 12 e61, published 2002.*
Miller et al., "Antibody microarray profiling of human prostate cancer sera: Antibody screening and identification of potential biomarkers", Proteomics, 2003, vol. 3, pp. 56-63.*
International Search Report dated May 20, 2014, issued in International Application No. PCT/US2014/017474.
Written Opinion of the International Searching Authority dated May 20, 2014, issued in International Application No. PCT/US2014/017474.
Notification Concerning Transmittal of International Preliminary Report on Patentability (Chapter I of the Patent Cooperation Treaty) dated Sep. 3, 2015, issued in International Application No. PCT/US2014/017474.
Barone, et al. "Modulation of single-walled carbon nanotube photoluminescence by hydrogel swelling." Acs Nano 3.12 (2009): 3869-3877.

* cited by examiner

SENSOR FOR DETECTING ANALYTES

PRIORITY CLAIM

This application claims priority to U.S. Provisional Application No. 61/767,516, filed Feb. 21, 2013, which is incorporated by reference in its entirety.

TECHNICAL FIELD

The present invention relates to a sensor for detecting analytes.

BACKGROUND

On-line analytical technology for the production recombinant proteins is an area of great interest. Product titer and post-translational modifications are important process parameters to be monitored. Some post-translational modifications, such as glycosylation patterns, can change in response to changes in process conditions (e.g., media components, temperature, pH, $pCO_2$, dissolved oxygen, cell density, duration, and others) and can have a dramatic effect on the properties of the protein product (e.g., pharmacokinetics and immunogenicity of a protein drug). Current analytical technologies for determining titer and glycosylation, such as ELISA and tandem LC/MS systems, respectively, can deliver detailed information but are costly in terms of time, reagents, and multiplexing capabilities. Furthermore, these methods are incompatible with on-line process use.

SUMMARY

In general, a sensor can include a hydrogel and a photoluminescent nanostructure.

In one aspect, a sensor for detecting an analyte can include a substrate hydrogel arranged on a support, a sensor hydrogel arranged on the substrate hydrogel, a photoluminescent nanostructure embedded in the sensor hydrogel, and an analyte-binding compound associated with the photoluminescent nanostructure.

In some embodiments, the sensor can also include a linker, wherein the analyte-binding compound can be associated with the photoluminescent nanostructure via the linker. The linker can be associated with the nanostructure by a non-covalent interaction. The linker can also include a polymer. The polymer can include a polypeptide, a polynucleotide or a polysaccharide. The polysaccharide can be chitosan.

In some embodiments, the polymer can be crosslinked, thereby providing clusters of photoluminescent nanostructures.

In some embodiments, the linker can include a first binding partner, and the analyte-binding protein can include a second binding partner, selected such that the first binding partner and second binding partner bind together. The first binding partner can include a metal ion. The linker can include a chelating region. In some embodiments, the analyte-binding compound can be an analyte-binding protein.

In some embodiments, the substrate hydrogel can include poly(acrylamide). In some embodiments, the sensor hydrogel can include poly(acrylamide).

In another aspect, a method of making a sensor for detecting an analyte can include arranging a substrate hydrogel on a support, casting a sensor hydrogel from a sensor hydrogel precursor composition on the substrate hydrogel, wherein the sensor hydrogel precursor composition can include a photoluminescent nanostructure in the sensor hydrogel, and an analyte-binding compound associated with the photoluminescent nanostructure.

In some embodiments, arranging the substrate hydrogel on the support can include casting the substrate hydrogel from a substrate hydrogel precursor composition on the support. In some embodiments, the substrate hydrogel can include poly(acrylamide). In some embodiments, the sensor hydrogel can include poly(acrylamide).

In another aspect, a method of detecting an analyte can comprise contacting a composition including an analyte to a sensor including: a substrate hydrogel arranged on a support, a sensor hydrogel arranged on the substrate hydrogel, a photoluminescent nanostructure embedded in the sensor hydrogel, and an analyte-binding compound associated with the photoluminescent nanostructure.

In some embodiments, the method of detecting the analyte can further include detecting photoluminescence from the photoluminescent nanostructure. Detecting photoluminescence can include focusing an objective on the sensor hydrogel.

Other aspects, embodiments, and features will be apparent from the following description, the drawings, and the claims.

BRIEF DESCRIPTION OF THE DRAWINGS

FIG. 4A presents images of an engineered HEK cell line that is transfected to produce both murine IgG (TA99) and GFP. FIG. 4B shows sensor response to control and IgG cell line extract as well as series dilution of a 4 day culture. IgG concentrations determined by ELISA and calibration curve presented in the insert. FIG. 4C shows sensor response to CHO cell culture (days 1-4) growth and media as control. IgG concentrations determined by ELISA and calibration curve presented in the insert. FIG. 4D illustrates an alternative method of suppressing background protein signal by mapping modulation after addition and after washing step, thus revealing weakly bound, unspecific species (below the red line).

FIG. 6A presents qualitative images of control and IgG producing cells showing colocalization of SWNT response. FIG. 6B shows location of top 1000 SWNT in IgG and control cell images, presented as coverage percentage of cell area (specific) and gel area (non-specific) in each image. FIG. 6C shows exemplary cell images. FIG. 6D shows dynamic response of SWNT sensors to IgG producing cells plated on gel presented as distributions of top 1000 SWNT from images and micrographs of scaled SWNT intensity. FIG. 6E illustrates mapping visible IgG producing cell islands, the colocalized SWNT signal underneath, and ranking the islands' productivity based on intensity normalized by island area.

FIG. 7A shows SEM images of fluorescent SWNT clusters (slow dried sample—left panel) and some structural information of the structures (flash dried—right panel). FIG. 7B shows absolute force indentation curves at 8 μm for each of the gel compositions. FIG. 7C shows normalized force relaxation curves for PRI analysis and resulting pore size calculations. FIG. 7D shows elution profiles of different diameter FITC-coated dextran particles from the gel.

DETAILED DESCRIPTION

Figure 1A:
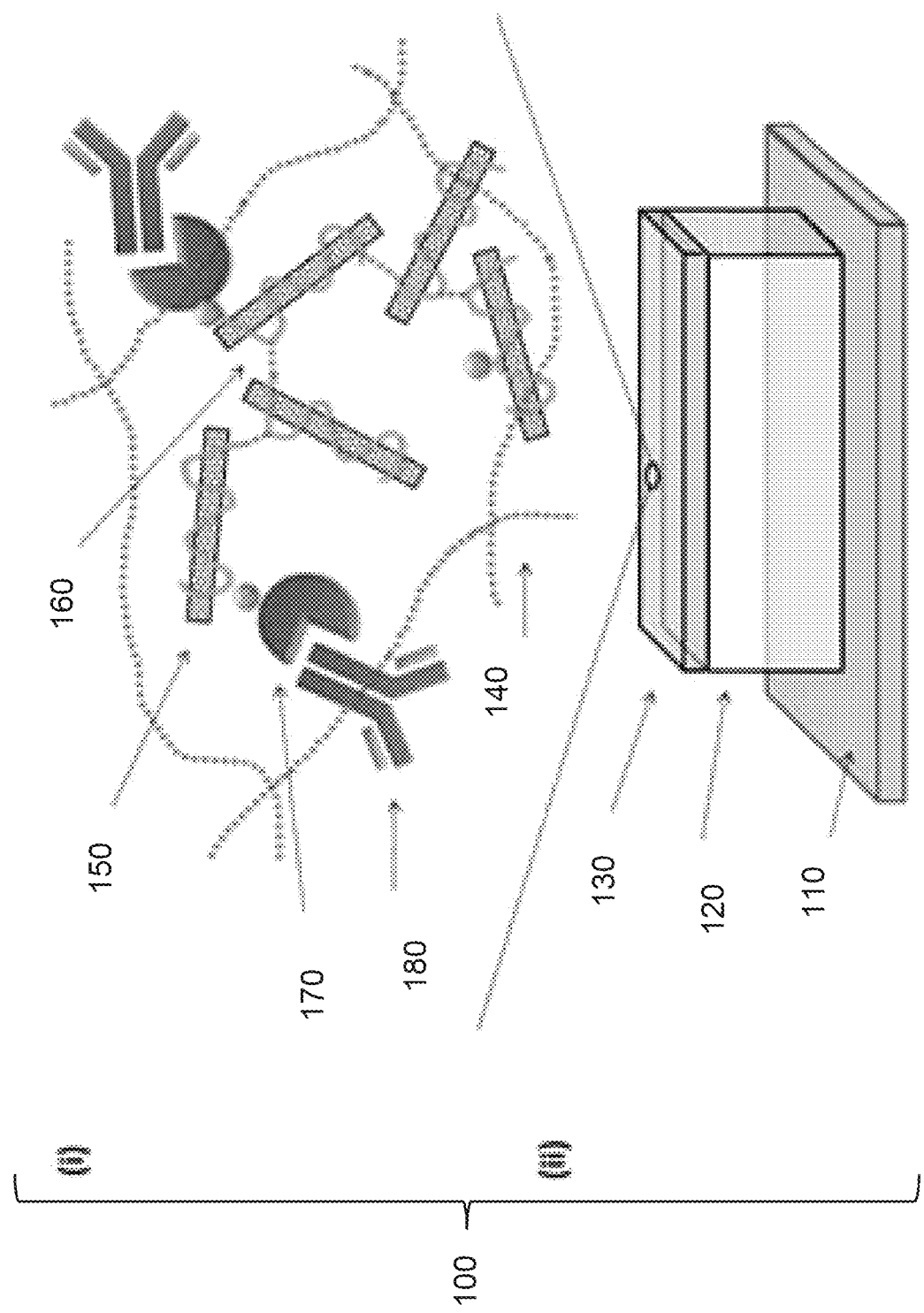
FIG. 1A is a schematic illustration of a sensor for the detection of an analyte.

Sensors including hydrogels and photoluminescent nanostructures are described, as well as systems and methods using the sensors. The photoluminescent nanostructures are associated with analyte-binding compounds. Binding of the analyte to the analyte-binding compound changes the photoluminescent properties of the photoluminescent nanostructures. Thus, the presence or absence of the analyte can be determined based on the observed photoluminescent properties of the photoluminescent nanostructures. The change in the photoluminescence can include a change in photoluminescence intensity, a change in peak wavelength, a Raman shift, or a combination thereof.

In some cases, detection of analytes with photoluminescent nanostructures can be limited by the presence of non-specific background photoluminescence. Background photoluminescence can arise from, among other sources, a support that underlies the photoluminescent nanostructures, e.g., supports including glass or plastic. One way to minimize background photoluminescence is to use a support composed of highly purified materials that are free of contaminants that may be responsible for the background photoluminescence. However, the use of such materials can increase the cost and complexity of analyte detection.

Another method to avoid background photoluminescence is to use a detection system that does not detect the background photoluminescence. In such a system, substrates that suffer from background photoluminescence can nonetheless be used, because the detection system detects only photoluminescence distinct from the background photoluminescence. In some cases, this might be achieved with appropriate sets of wavelength filters. However, if the background photoluminescence and the photoluminescence arising from the photoluminescent nanostructures occur at overlapping wavelengths, filters may not be able to reject a sufficient amount of the background photoluminescence while still allowing a sufficient amount of the photoluminescence arising from the photoluminescent nanostructures to pass.

It can be advantageous to use a detection system that rejects background photoluminescence on the basis of spatial configuration rather than on the basis of wavelength. One way to accomplish this is to use an optical detection system that provides a distinct focal plane, where the detected photoluminescence is substantially from sources in the focal plane. Photoluminescent sources outside the focal plane are not detected by the detector. In this way, the detector does not suffer from issues associated with background photoluminescence.

Thus, a sensor for detecting an analyte can be arranged on a support. Photoluminescence from the sensor is detected by an optical system that detects photoluminescence substantially only from sources in the focal plane. Sources outside the focal plane do not contribute substantially to the detected photoluminescence. When the sensor is arranged directly on the support, the focal plane may extend outside the boundaries of the sensor and include a portion of the support. In this situation, background photoluminescence will be detected. Rather than being arranged directly on the support, the sensor can be arranged on an intermediate substrate. The intermediate substrate, in turn, is in contact with the support. The intermediate substrate separates the sensor from the support, such that the focal plane does not include any portion of the support. The intermediate substrate can be advantageously composed of materials that are substantially free of background photoluminescence. The intermediate substrate can be advantageously composed of materials that are compatible with the sensor. For example, the sensor can include a hydrogel, and the intermediate substrate can also include a hydrogel.

With reference to FIG. 1A, sensor 100 includes (illustrated in lower panel (ii)) support 110 which supports substrate hydrogel 120, which in turn supports sensor hydrogel 130. Sensor hydrogel 130 (detailed in upper panel (i)) includes hydrogel network 140, photoluminescent nanostructures and associated linking polymers 150, optional crosslinks 160 between linking polymers 150, and analyte-binding compound 170. In FIG. 1A, sensor hydrogel 130 is illustrated with analyte 180 being associated with analyte-binding compound 170, though it will be understood that sensor hydrogel 130 will typically be formed in the absence of analyte 180, and analyte 180 may be contacted with sensor hydrogel 130 after formation. Thus in some states, sensor gel 130 is free of analyte 180 and in other states includes analyte 180 (e.g., associated with analyte-binding compound 170). The presence of the analyte 180 alters the photoluminescent properties of the photoluminescent nanostructures.

Figure 1B:
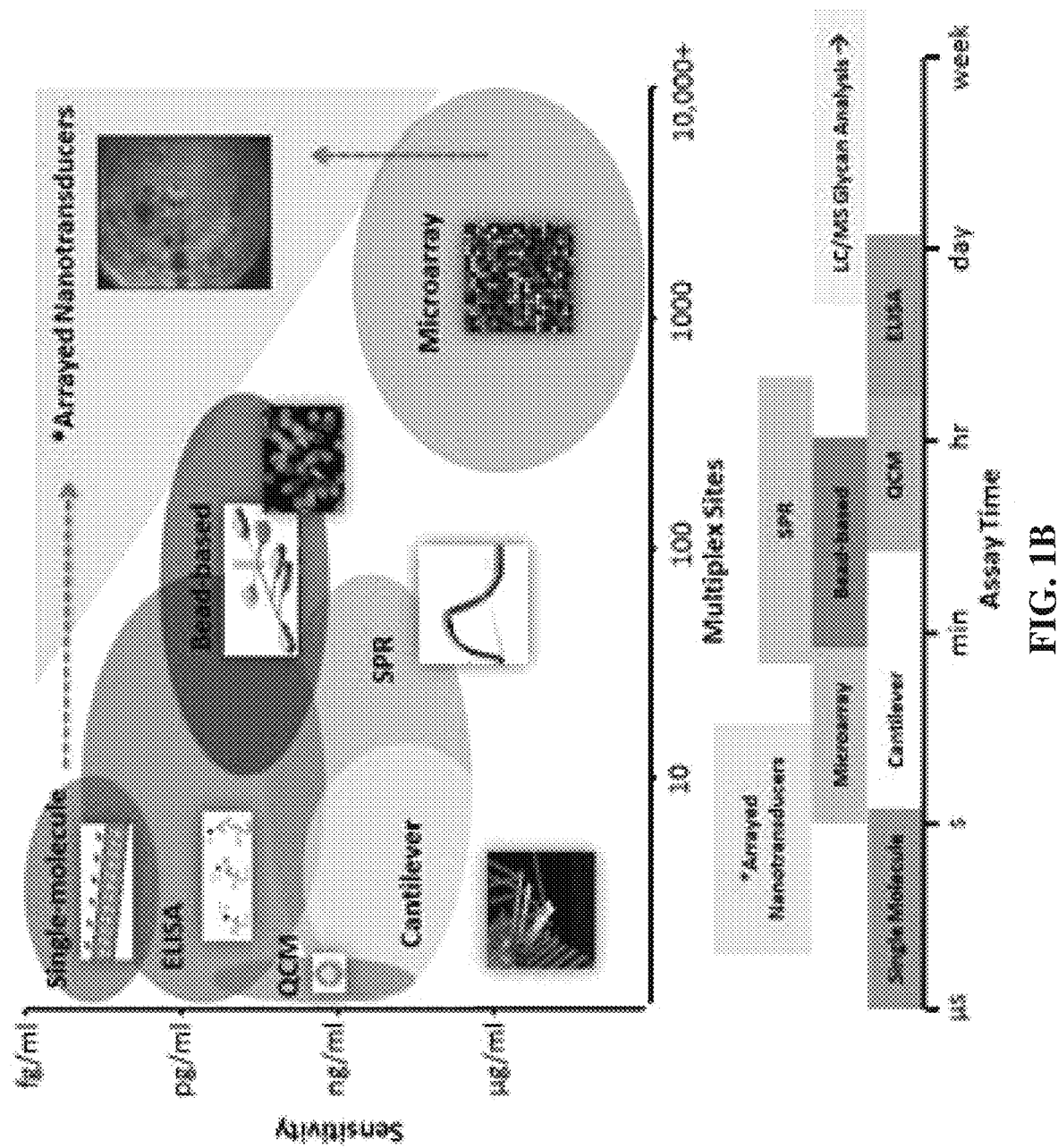
FIG. 1B illustrates existing technologies used for protein and glycan analysis and the competitive space filled by nanosensor arrays.

On-line analytical technology for the rapidly growing production of clinical recombinant antibodies is an area of great interest. See, e.g., Henriques, J. G., et al. in *Optical Sensor Systems in Biotechnology*, Vol. 116. (ed. G. Rao) 73-972009); Pizarro, S. A., et al. *Biotechnology and Bioengineering* 104, 340-351 (2009); and Rodrigues, M. E., et al. *Biotechnology Progress* 26, 332-351 (2010); each of which is incorporated by reference in its entirety. Product titer is an important process parameter, as is information about post-translational modification of the product (such as glycosylation patterns). These patterns can change due to changes in processing conditions (e.g., media components, temperature, pH, $pCO_2$, dissolved oxygen, cell density, duration, and others) and can have a dramatic effect on the pharmacokinetics and immunogenicity of the resulting drug. Current analytical technologies for determining titer and glycosylation, such as ELISA and tandem LC/MS systems, respectively, can deliver detailed information at the expense of time, reagent, and multiplexing capabilities (FIG. 1B). Furthermore, their processing steps are prohibitive to any on-line process use. The trend to milliliter sized bioreactors for upstream process optimization will also require platforms that can accurately assay much lower protein and glycan quantities. Emerging nanoengineered sensor platforms that do not require fluorescent labeling or glycan liberation steps may be the solution to rapid, sensitive, and highly-multiplexed analytics of proteins and glycans (FIG. 1B; see Reuel, N. F., et al. *Chemical Society Reviews* 41, 5744-5779 (2012), which is incorporated by reference in its entirety). Carbon-nanotube based optical sensors for single protein and single glycan detection have been described (see Ahn, J. H. et al. *Nano Letters* 11, 2743-2752 (2011); and Reuel, N. F. et al. *J. Am. Chem. Soc.* 133, 17923-17933 (2011); each of which is incorporated by reference in its entirety). These tools, combined with a hydrogel platform, can be used for analysis of macroscale biomanufactured products.

Some embodiments can be particularly advantageous due to the biocompatible nature of hydrogels. Hydrogels are particularly resistant to biological fouling. When sensors are used in vitro, biological entities (e.g., endothelial cells, proteins, etc.) may adhere to the sensor and block and/or consume the compound to be detected (e.g., glucose). When this occurs, the sensor may fail to detect the presence of the compound, or may detect a concentration of the compound that is lower than the amount in the surrounding fluid (e.g., blood), thus rendering the sensor inaccurate or unusable. Because hydrogels can be resistant to biological fouling, such disadvantages can be mitigated. In addition, in some embodiments where the hydrogels are not biodegradable, undesired leaching of nanostructures may be prevented.

As used herein, the term "hydrogel" is given its ordinary meaning in the art and refers to a material comprising a polymer network that is able to trap and contain water. The hydrogel may include polymer chains that are crosslinked, either directly or via a crosslinking agent. The degree of crosslinking may be varied, in some cases, to tailor the extent to which the gel absorbs or retains fluids. Examples of polymers capable of forming hydrogels include, but are not limited to, collagen, silicon-containing polymers, polyacrylamides, crosslinked polymers (e.g., polyethylene oxide, polyAMPS and polyvinylpyrrolidone), polyvinyl alcohol, acrylate polymers (e.g., sodium polyacrylate), and copolymers with an abundance of hydrophilic groups.

The hydrogel can be a porous structure. The pore sizes in the porous structure can be determined by factors including the concentration of polymers and crosslinks in the hydrogel. A hydrogel having a desired pore size or desired pore size distribution can be prepared by selecting the concentrations of monomers and crosslinkers present during polymerization to form a hydrogel. It can be advantageous for the hydrogel pores to be large enough to permit free access of analytes to components embedded in the hydrogel, e.g., to photoluminescent nanostructures. The pore size can be in the range of, for example, 10 nm to 1,000 nm, 20 nm to 500 nm, 50 nm to 250 nm, or 10 nm to 100 nm. When the analyte is a macromolecule (e.g., a protein, such as an immunoglobulin), a pore size greater than 10 nm, greater than 20 nm, greater than 30 nm, greater than 40 nm, greater than 50 nm, greater than 60 nm, greater than 70 nm, greater than 80 nm, greater than 90 nm, or 100 nm or greater can be desirable.

As used herein, the term "nanostructure" refers to articles having at least one cross-sectional dimension of less than about 1 µm, less than about 500 nm, less than about 250 nm, less than about 100 nm, less than about 75 nm, less than about 50 nm, less than about 25 nm, less than about 10 nm, or, in some cases, less than about 1 nm Examples of nanostructures include nanotubes (e.g., carbon nanotubes), nanowires (e.g., carbon nanowires), graphene, and quantum dots, among others. In some embodiments, the nanostructures include a fused network of atomic rings.

A "photoluminescent nanostructure," as used herein, refers to a class of nanostructures that are capable of exhibiting photoluminescence. Examples of photoluminescent nanostructures include, but are not limited to, single-walled carbon nanotubes ("SWNT"), double-walled carbon nanotubes, semi-conductor quantum dots, semi-conductor nanowires, and graphene, among others. In some embodiments, photoluminescent nanostructures exhibit fluorescence. In some instances, photoluminescent nanostructures exhibit phosphorescence.

If the nanostructure is a carbon nanotube, the carbon nanotube can be classified by its chiral vector (n,m), which can indicate the orientation of the carbon hexagons. The orientation of carbon hexagons can affect interactions of the nanotube with other molecules, which in turn, can affect a property of the nanostructure.

A linker can be associated with the nanostructure. The association can be a bond, for example, a covalent, ionic, van der Waals, dipolar or hydrogen bond. The association can be a physical association. For example, at least a portion of the nanostructure can be embedded in the polymer or a portion of the polymer can encompass the nanostructure.

A linker can include a polymer. A polymer can include a polypeptide, a polynucleotide or a polysaccharide. Examples of polysaccharides include dextran and chitosan. A polymer can include a plastic, for example, polystyrene, polyamide, polyvinyl chloride, polyethylene, polyester, polypropylene, polycarbonate, polyacrylamide or polyvinyl alcohol.

A polymer can be biocompatible, which can mean that the polymer is well tolerated by an organism. More specifically, biocompatibility can mean that a polymer does not elicit an immune response when it is brought in contact with an organism. It can also mean that a polymer can integrate into cell structures, cells, tissues or organs of an organism. The organism can be mammal, in particular, a human.

An exemplary polymer can exhibit minimal binding with other molecules. In certain circumstances, a polymer can have a protein adsorption of less than 5 µg/cm$^2$, less than 1

μg/cm², less than 0.5 μg/cm², less than 0.1 μg/cm², less than 0.05 μg/cm², or less than 0.01 μg/cm².

The association of a linker with a nanostructure can change a property of the nanostructure. The property can be conductivity, polarity, or resonance. The property can be photoluminescence, including fluorescence or phosphorescence. More specifically, the property can be fluorescence with a wavelength in the near infrared spectrum. The property can be an emission wavelength, an emission intensity, a conductance, an electromagnetic absorbance or an emittance.

A linker can be configured to interact with an analyte-binding compound. The analyte-binding compound undergoes a specific and typically reversible binding with an analyte. One class of suitable analyte binding compounds are proteins. In particular, proteins that undergo specific and typically reversible binding with an analyte (referred to herein as "capture proteins") can be suitable.

A capture protein can include a protein, a polypeptide or a peptide. In some cases, a capture protein can be a complex of proteins. A capture protein can also include a full length protein, a fragment of a protein or a protein domain. A capture protein can be a fusion protein, which can include portions originating from one protein or portions originating from more than one protein. A capture protein can include a protein tag or marker. A capture protein can also be modified, for example, by glycosylation, ubiquitination, PEGylation, SUMOylation or biotinylation. A capture protein can be synthesized from a nucleic acid sequence that was amplified from a cDNA library, genomic DNA, a DNA vector or plasmid, or a DNA fragment.

The number of linkers associated with the nanostructure present in the analysis region can exceed the number of capture proteins. More specifically, the number of capture protein binding sites on linkers associated with a nanostructure can exceed the number of capture proteins. The ratio of capture protein binding sites on linkers associated with a nanostructure to capture proteins can be greater than 1.1 to 1, greater than 1.5 to 1, greater than 2 to 1, greater than 5 to 1, or greater than 10 to 1. Having an excess of capture protein binding sites on linkers associated with a nanostructure can minimize the amount of unbound capture protein in a sample. Unbound capture proteins within the sample can compete with capture proteins bound to the composition for binding to the analyte. This can affect the accuracy and/or precision of the analyte detection. Having an excess of capture protein binding sites on linkers associated with a nanostructure can also increase the analyte concentration range over which analyte can be accurately detected because the saturation limit of the binding sites is increased.

The interaction between the linker and the capture protein can be binding to a capture protein. The linker can be configured to interact with a capture protein by including a first binding partner in the linker that can interact with the capture protein. The first binding partner can be known binding partner of the capture protein or a portion thereof. The first binding partner can include an ion. The ion can be a metal ion. The metal ion can be a nickel, iron, cadmium, copper, magnesium, calcium, arsenic, lead, mercury or cobalt ion (e.g. $Ni^{2+}$, $Fe^{2+}$, $Cd^{2+}$, $Cu^{2+}$, $Mg^{2+}$, $Ca^{2+}$, $As^{2+}$, $Pb^{2+}$, $Hg^{2+}$ or $Co^{2+}$). The first binding partner can include a protein, a nucleotide, a saccharide, a lipid or combinations thereof. See, for example, WO 2012/030961, which is incorporated by reference in its entirety.

A linker can further include a chelating region. A chelating region can include a chelator, which can be a polydentate ligand capable of forming two or more bonds with a single central atom. A chelator can include one or more carboxylate ions. For example, a linker can include $N_\alpha,N_\alpha$-bis(carboxymethyl)-L-lysine (NTA). A chelator can bind to a first binding partner (e.g. a metal ion) in order to incorporate the first binding partner into a linker.

The ion can act a proximity quencher of photoluminescent nanostructure. In particular, the ion can quench near infrared fluorescence. The quenching can be reversible. The quenching can also depend on the distance between the nanostructure and the ion. In other words, as the distance between the nanostructure and the ion changes, the photoluminescence from the nanostructure can also change. Generally, as the distance between the ion and the nanostructure decreases, the amount of photoluminescence quenching can increase.

In some embodiments, the capture protein can include a second binding partner, such that the first binding partner and second binding partner can bind together. The second binding partner can be an endogenous motif or endogenous domain within a capture protein. Alternatively, the second binding partner can be added to a capture protein. In some embodiments, the second binding partner can be a protein tag. A protein tag can be a peptide sequence grafted onto a protein, which can be used for separating (e.g. using tag affinity techniques), increasing solubility, immobilizing, localizing or detecting a protein. The protein tag can be a histidine tag, chitin binding protein tag, maltose binding protein tag, glutathione-S-transferase tag, c-myc tag, FLAG-tag, V5-tag or HA-tag. One method for adding a second binding partner to a capture protein can include using primers including the sequence encoding for the second binding partner to PCR amplify DNA encoding for the capture protein. A second method can include cloning DNA encoding for the capture protein into an expression vector designed to produce a fusion of the capture protein and the second binding partner.

Binding of a first and a second binding partner can be selective binding, which can provide the selectivity needed to bind to the corresponding binding partner (or relatively small group of related molecules or proteins) in a complex mixture. The degree of binding can be less than 100%, less than 90%, less than 80%, less than 70%, less than 60%, less than 50%, less than 40%, less than 30%, less than 20% or less than 10% of a second binding partner present binding to a first binding partner. The degree of binding can be more than 10%, more than 20%, more than 30%, more than 40%, more than 50%, more than 60%, more than 70%, more than 80% or more than 90% of a second binding partner present binding to a first binding partner. A first binding partner and a second binding partner can bind with a dissociation constant less than 1 mM, less than 0.1 mM, less than 0.01 mM, less than 1 μM, less than 0.1 μM, or less than 0.01 μM. A first binding partner and a second binding partner can bind with a dissociation constant greater than 1 nm, greater than 0.01 μM, greater than 0.1 μM, greater than 1 μM, greater than 0.01 mM, or greater than 0.1 mM.

The linker can also be configured to interact with a capture protein by including a region capable of chemically reacting with the capture protein. The chemical reaction can form a covalent, ionic, van der Waals, dipolar or hydrogen bond between the linker and the capture protein.

The interaction of a capture protein with a linker associated with a nanostructure can change a property of the nanostructure. The property can be conductivity, polarity, or resonance. The property can be photoluminescence, including fluorescence or phosphorescence. The photoluminescence can be fluorescence with a wavelength within the near infrared spectrum. The property can be an emission wavelength, an emission intensity, a conductance, an electromagnetic absorbance or an emittance.

Without intending to be bound by any particular mechanism, the change in the property can be caused by a change in the distance between an ion in the first binding partner and the nanostructure. As the distance between the nanostructure and the ion changes, a nanostructure property can also change. For example, as the distance between the nanostructure and the ion changes, nanostructure photoluminescence can also change. When the capture protein binds to the linker, the distance between the ion and nanostructure can change, which can alter the nanostructure photoluminescence. Generally, as the distance between the ion and the nanostructure decreases, the amount of photoluminescence quenching can increase.

In some embodiments, a composition can further include a capture protein, which can be configured to specifically interact with at least one analyte. In particular, the capture protein can be configured to specifically bind to at least one analyte. Specific binding can be more limited than selective binding. Specific binding can be used to distinguish a binding partner from most other chemical species except optical isomers, isotopic variants and perhaps certain structural isomers. The degree of binding can be less than 100%, less than 90%, less than 80%, less than 70%, less than 60%, less than 50%, less than 40%, less than 30%, less than 20% or less than 10% of an analyte present binding to a capture protein. The degree of binding can be more than 10%, more than 20%, more than 30%, more than 40%, more than 50%, more than 60%, more than 70%, more than 80% or more than 90% of an analyte present binding to a capture protein. An analyte and a capture protein can bind with a dissociation constant less than 1 mM, less than 0.1 mM, less than 0.01 mM, less than 1 μM, less than 0.1 μM, or less than 0.01 μM. An analyte and a capture protein can bind with a dissociation constant greater than 1 nm, greater than 0.01 μM, greater than 0.1 μM, greater than 1 μM, greater than 0.01 mM, or greater than 0.1 mM.

The interaction of an analyte with a capture protein that is interacting with a linker associated with a nanostructure can change a property of the nanostructure. The property can be conductivity, polarity, or resonance. The property can be photoluminescence, including fluorescence or phosphorescence. More specifically, the property can be a fluorescent emission within the near infrared spectrum. The property can be an emission wavelength, an emission intensity, a conductance, an electromagnetic absorbance or an emittance.

The interaction of an analyte with a capture protein can be reversible, meaning that the analyte can bind to the capture protein and then release and be free of binding. The change in a property of the nanostructure due to the interaction of an analyte with a capture protein can also be reversible. For example, the property of a nanostructure can have a first value, the analyte can bind to the capture protein and alter the property to a second value, then the analyte can release from the capture protein and the property can return to the first value.

The analyte can be a small molecule, protein, biomolecule, drug, biologic, or a metabolite thereof. For example, the analyte can be a monosaccharide, a polysaccharide, an amino acid, peptide, polypeptide, protein, a nucleotide, an oligonucleotide, a lipid, a polylipid, or a combination thereof. As one example, the analyte can be immunoglobulin G (IgG) and the capture protein can be selected to specifically bind IgG. In this case, the capture protein can be, for example, protein A or *Pisum sativum* agglutinin (PSA).

A method of detecting protein binding can include determining the presence of an analyte in the sample based on the monitored property. Determining the presence of an analyte can include evaluating when the analyte is absent. In some embodiments, determining the presence of an analyte can include determining the concentration of the analyte, determining the purity of the analyte or determining the quantity of the analyte. In some embodiments, relatively low concentrations or quantities of an analyte can be determined. The ability to determine low concentrations of an analyte may be useful, for example, in detecting trace pollutants or trace amounts of toxins within a subject. In some embodiments, analyte concentrations of less than about 100 micromolar, less than about 10 micromolar, less than about 1 micromolar, less than about 100 nanomolar, less than about 10 nanomolar, or less than about 1 nanomolar can be determined. The quantity of the analyte that can be determined can be less than 1 mole, less than 1 millimole, less than 1 micromole, less than 1 nanomole, less than 1 picomole, less than 1 femtomole, less than 1 attomole or less than 1 zeptomole. In some cases, a single molecule of an analyte can be determined. The purity of the analyte can be greater than 25% pure, greater than 50%, greater than 75% pure, greater than 80%, greater than 85% pure, greater than 90% pure, greater than 95% pure, greater than 99% pure or greater than 99.9% pure.

A linker can have a formula:

A-L-C, where A can include a polymer, where at least a portion of the nanostructure is embedded in the polymer, L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$ cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl and said hydrocarbon chain being optionally interrupted by O, S, N($R^a$), C(O), N($R^a$)C(O)O, OC(O)N($R^a$), N($R^a$)C(O)N($R^b$), C(O)O, or OC(O)O; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety.

The composition can include a chelator-containing compound, which can include a chelator region and a non-chelator region. C can be the chelator region. L can include the non-chelator region.

In some circumstances, A can include a polymer $[(M)_x(N)_y(Q)_z]_q$, where each of M, N and Q, independently, can be selected from the group consisting of a linear or cyclic $C_3$-$C_8$ hydrocarbyl, heterocyclyl, cyclyl, or aryl including one or more amine, alcohol or carboxylic acid group, where each M-N, M-Q or N-Q can include O, S, N($R^a$), C(O), N($R^a$)C(O)O, OC(O)N($R^a$), N($R^a$)C(O)N($R^b$), C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

—[—$X_1$—(C$R^aR^b$)$_n$—$X_2$—(C$R^aR^b$)$_o$—$X_3$—]— where each $X_1$, $X_2$ and $X_3$, can be O, S, N($R^a$), C(O), N($R^a$)C(O)O, OC(O)N($R^a$), N($R^a$)C(O)N($R^b$), C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$, and salts thereof, where G can be a bond, C, O, S, P, P=O or N; n is 0-6; and z and y can be selected to satisfy the valence requirements of G. In other preferred embodiments, the compound can have the formula,

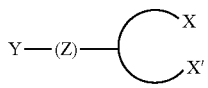

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

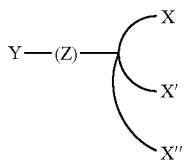

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)HNCH_2CH_2NH((CH_2)_nCOOH)$, $(HOOC(CH_2)_n)_2PCH_2CH_2P((CH_2)_nCOOH)_2$, $(HOOC(CH_2)_n)_2P(O)CH_2CH_2P(O)((CH_2)_nCOOH)_2$, $HSCH_2CH_2CH(SH)(CH_2)_4CONH(CH_2)_nCOOH$, where can is an integer between 1 and 10, or $N_\square,N_\square$-bis(carboxymethyl)-L-lysine.

In some embodiments, the composition can include a nanostructure and a linker having a formula:

A-L-C, where A can include the polymer covalently bonded to a portion of the nanostructure, L can be a linking moiety including a saturated or unsaturated $C_{4-10}$ hydrocarbon chain optionally containing at least two conjugated double bonds, at least one triple bond, or at least one double bond and one triple bond; said hydrocarbon chain being optionally substituted with $C_{1-4}$ alkyl, $C_{2-4}$ alkenyl, $C_{2-4}$ alkynyl, $C_{1-4}$ alkoxy, hydroxyl, halo, carboxyl, amino, nitro, cyano, $C_{3-6}$ cycloalkyl, 3-6 membered heterocycloalkyl, unsubstituted monocyclic aryl, 5-6 membered heteroaryl, $C_{1-4}$ alkylcarbonyloxy, $C_{1-4}$ alkyloxycarbonyl, $C_{1-4}$ alkylcarbonyl, or formyl and said hydrocarbon chain being optionally interrupted by O, S, $N(R^a)$, C(O), $N(R^a)C(O)O$, $OC(O)N(R^a)$, $N(R^a)C(O)N(R^b)$, C(O)O, or OC(O)O; each of $R^a$ and $R^b$, independently, being hydrogen, alkyl, alkenyl, alkynyl, alkoxy, hydroxylalkyl, hydroxyl, or haloalkyl, or L can be a bond, and C can be a metal ion complexing moiety.

The composition can include a chelator-containing compound, which can include a chelator region and a non-chelator region. C can be the chelator region. L can include the non-chelator region.

In some circumstances, A can include a polymer $[(M)_x(N)_y(Q)_z]_q$, where each of M, N and Q, independently, can be selected from the group consisting of a linear or cyclic $C_3-C_8$ hydrocarbyl, heterocyclyl, cyclyl, or aryl including one or more amine, alcohol or carboxylic acid group, where each M-N, M-Q or N-Q can include O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where each of x, y and z can be integers between 0 and 50, 0 and 20 or 0 and 10 and q can be an integer between 1 and 1000, 5 and 500, or 10 and 100.

In some circumstances, L can have the formula:

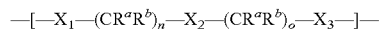

where each $X_1$, $X_2$ and $X_3$, can be O, S, $N(R^a)$, C(O), $N(R^a)C(O)O$, $OC(O)N(R^a)$, $N(R^a)C(O)N(R^b)$, C(O)O, or OC(O)O, each of $R^a$ and $R^b$, independently, can be hydrogen, alkyl, alkenyl, alkynyl, alkoxy, hydroxylalkyl, hydroxyl, or haloalkyl, and where the value of n added to o can be 4 to 10.

In some circumstances, C can have the formula, $H_zG((CH_2)_nCO_2H)_y$, and salts thereof, where G can be a bond, C, O, S, P, P=O or N; n is 0-6; and z and y can be selected to satisfy the valence requirements of G. In other preferred embodiments, the compound can have the formula,

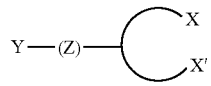

where X and X' can be the same or different and can be metal binding groups including atoms selected from the group of O, S, N, P or O=P, including carboxyl; Y can be bond, C, O, S, P, P=O or N; and Z can be a hydrocarbon having a backbone of one to six atoms, such as an alkyl group or alkenyl group. Each of X and X' can include other substituents in order to satisfy the valence requirements, such as for example, amine, thiol, phosphine or phosphine oxide, substituted by hydrogen or other organic moieties. In addition, the atoms bridging X and X' can be selected to form a 5-membered to 8-membered ring upon coordination to the metal ion. The bridging atoms can typically be carbon, but may be other elements, such as oxygen, nitrogen, or sulfur.

In yet another preferred embodiment, the compound can have the formula,

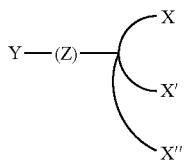

where X, X' and X" can be the same or different and can be metal binding groups including atoms selected from the group of O, S, N, P or O=P, including carboxyl; Y can be a bond, C, O, S, P, P=O or N; and Z can be a hydrocarbon having a backbone of one to six atoms, such as an alkyl group or alkenyl group. Each of X, X' and X" can include other substituents in order to satisfy the valence requirements, such as for example, amine, thiol, phosphine or phosphine oxide, substituted by hydrogen or other organic moieties. In addition, the atoms bridging X and X', X and X" or X' and X" can be selected to form a 5-membered to 8-membered ring upon coordination to the metal ion. The bridging atoms can typically be carbon, but may be other elements, such as oxygen, nitrogen, or sulfur. For example, C can be derived from $HSCH_2CH_2CH(SH)(CH_2)_nCOOH$, $H_2CH_2H_2CH(NH_2)(CH_2)_nCOOH$, $(HOOC(CH_2)_n)$ $HNCH_2CH_2NH((CH_2)_nCOOH)$, $(HOOC(CH_2)_n)_2$ $PCH_2CH_2P((CH_2)_nCOOH)_2$, $(HOOC(CH_2)_n)_2P(O)$ $CH_2CH_2P(O)((CH_2)_nCOOH)_2$, $HSCH_2CH_2CH(SH)(CH_2)_4$ $CONH(CH_2)_nCOOH$, where can is an integer between 1 and 10, or $N_\square,N_\square$-bis(carboxymethyl)-L-lysine.

Compounds can be prepared according to published procedures such as those described, for example, in Parameswara et al., Synthesis, 815-818 (1980) and Denny et al., J. Org. Chem., 27, 3404 (1962).

A sensor array can include a plurality of analysis regions on a support. A support can be glass or plastic. An analysis region can be a divot, a tube, a tray, a well, or a similar compartment for suitable for containing a liquid sample. In some cases, an analysis region can include a droplet or spot on the surface of a support (e.g., a flat support). In those cases, an analysis region can be formed by spotting the composition on a support. A plurality of analysis regions can be arranged in a pattern on a support. A pattern can include concentric circles, a spiral, a row, a column or a grid.

In some embodiments, the plurality of analysis regions can include two or more subsets of analysis regions. For example, a first subset of analysis regions can differ from a second subset of analysis regions by including a different nanostructure, a different linker, a different binding partner, a different capture protein, a different analyte or a different sample. Additionally, a first subset of analysis regions can differ from a second subset of analysis regions by including a different environmental factor including a buffer, a reagent, a nutrient, a serum, an exposure to light, an oxygen concentration, a temperature or a pH.

EXAMPLES

Results and Discussion
Sensor Fabrication and Detection Method
A polyacrylamide hydrogel matrix (FIG. 1A) in a specific multilayer configuration provides pore sizes (60 to 90 nm) that can be suitable for sensitive and selective antibody quantification. Polyacrylamide gel networks, (Ruchel, R., et al., Journal of Chromatography 166, 563-575 (1978); and Wang, J., et al. Advanced Materials 20, 4482-4489 (2008); each of which is incorporated by reference in its entirety) used routinely for PAGE protein separations, have an additional advantage of suppressing antibody adsorption. The design includes a substrate gel 1 mm thick without the SWNT near-infrared fluorophore to suppress background and to shift the focal volume off of the glass microscope slide substrate, which typically contains fluorescent impurities. The active sensing element is a thin, porous, polyacrylamide gel matrix with SWNT sensors dispersed throughout as a capping layer on the substrate gel. The matrix and configuration differ substantially from those developed for protein-protein interactions and glycoproteins (Ahn, J. H. et al. Nano Letters 11, 2743-2752 (2011); Reuel, N. F. et al. J. Am. Chem. Soc 133, 17923-17933 (2011), each of which is incorporated by reference in its entirety), as antibody analytes were found to have a substantially higher tendency for non-specific adsorption, and required larger pore sizes to overcome diffusion limitations.

Figure 1C:
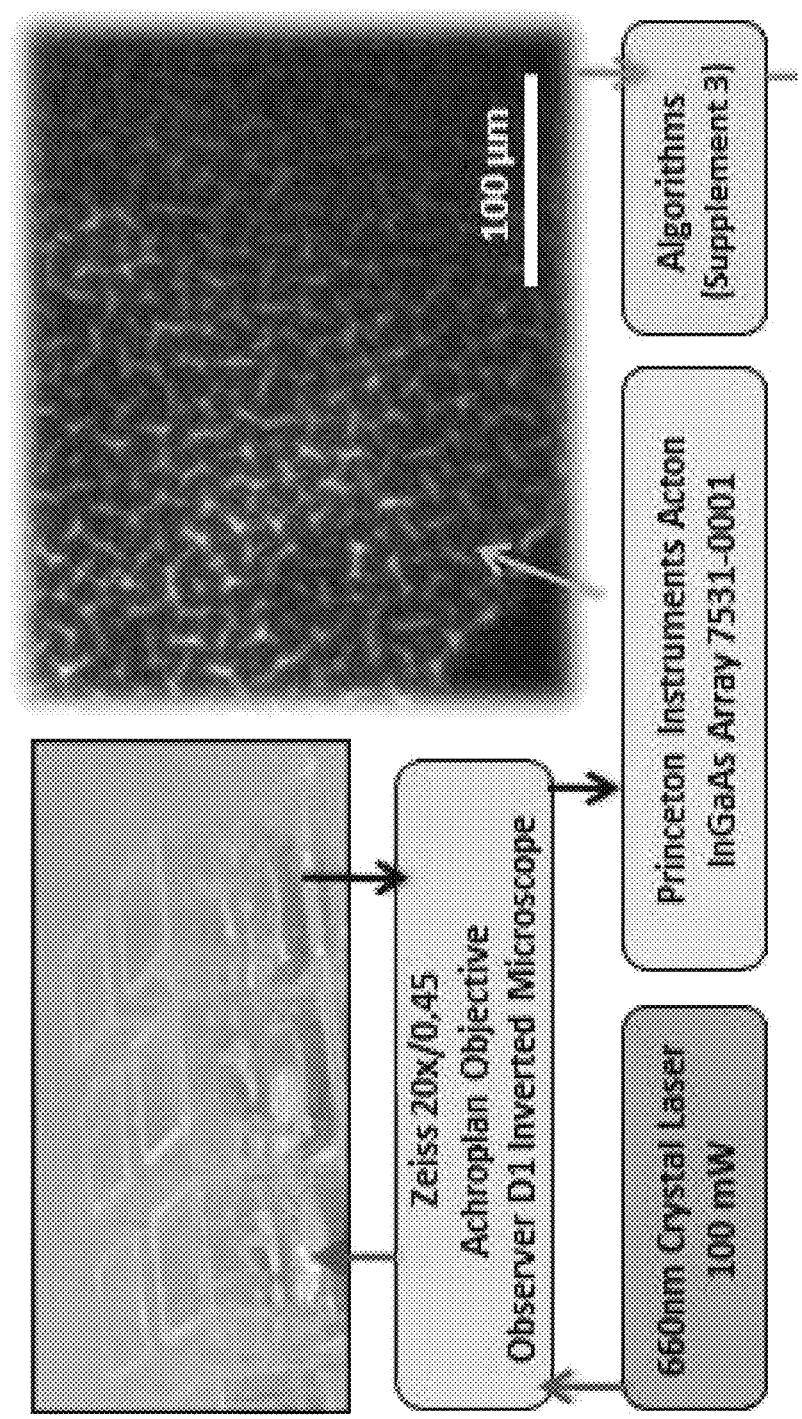
FIG. 1C illustrates a system for detecting an analyte. Hydrogel-based sensors were cast in wells. A microscope objective (20×) was used to assay the photoluminescence using excitation from a 660 nm laser. Emission was detected with a 2D InGaAs array.
Figure 1D:
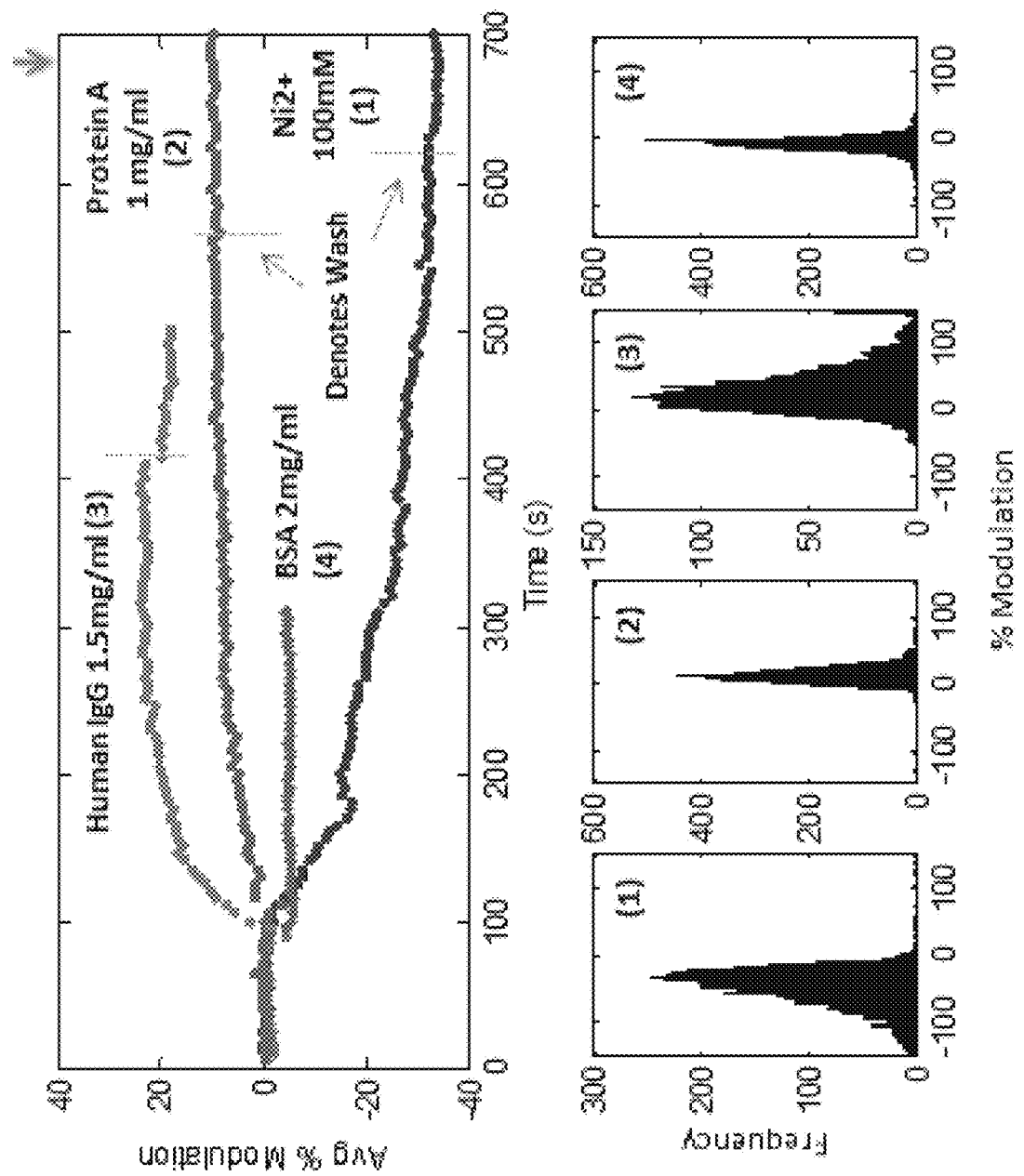
FIG. 1D illustrates the response of the sensor to nickel, Protein A, Human IgG, and BSA, presented as averaged curves and distributions of all SWNT sites.

For this work the sensor elements were chitosan-wrapped SWNT that had been chemically modified to display chelated nickel groups (see Reuel, N. F. et al. J. Am. Chem. Soc 133, 17923-17933 (2011), which is incorporated by reference in its entirety). The hydrophobic SWNT were wrapped in chitosan, a naturally-occurring amphiphilic polymer (oligiosacharide of N-Acetylglucosamine), to keep them stable and separate in solution. Unwrapped SWNT form tight bundles and their optical properties are diminished. The sensors were mixed and immobilized in a polyacrylamide gel. A polyacrylamide gel network can be advantageous because it has no reactive amine side groups, therefore, the nickel-chelated modification occurred only on the SWNT wrapping. As a result, the conjugated sensor proteins (Protein A and PSA Lectin) were localized and the overall signal transduction was increased. The gels were cast in 400 wells, excited by a 650 nm laser, and assayed on an inverted microscope with a 20× objective (FIG. 1C). The emission was collected on a 2D InGaAs array (Princeton Instruments) providing a spatial image of the SWNT array. An image processing algorithm tracked the temporal intensity of each array element in real time. The average fluorescent intensity (I) of all such elements in the field of view of the objective was defined as the ensemble response of the array. The response of each sensor as defined as percent modulation $(I_{Final}-I_{Before\ Add}/I_{Before\ Add})$ where $I_{Final}$ is the plateaued signal after analyte addition. Divalent nickel, protein A, and IgG addition (100 mM, 1 mg/ml, 1.5 mg/ml) caused a decrease, increase, and additional increase respectively (FIG. 1D). Subsequent washing of the gel surface showed negligible change in the ensemble signal, which was interpreted as absence of unbinding. Adding a BSA control (2 mg/ml) did not elicit a sensor response.

In contrast to averaging the signal for each frame to create an ensemble response, one can analyze the response of each individual sensor element (SWNT pixel cluster) to reveal a more complete and detailed picture of the response distribution (FIG. 1D). Not all sensors were equally responsive; within the SWNT array there was a sub-population of 'strong responders.' These were likely clusters that had better access to the analyte or had been more completely functionalized with the sensor proteins. When sensor response was plotted versus starting intensity it was clear that the best modulators were those that had the lowest starting intensity at the onset.

Figure 2A:
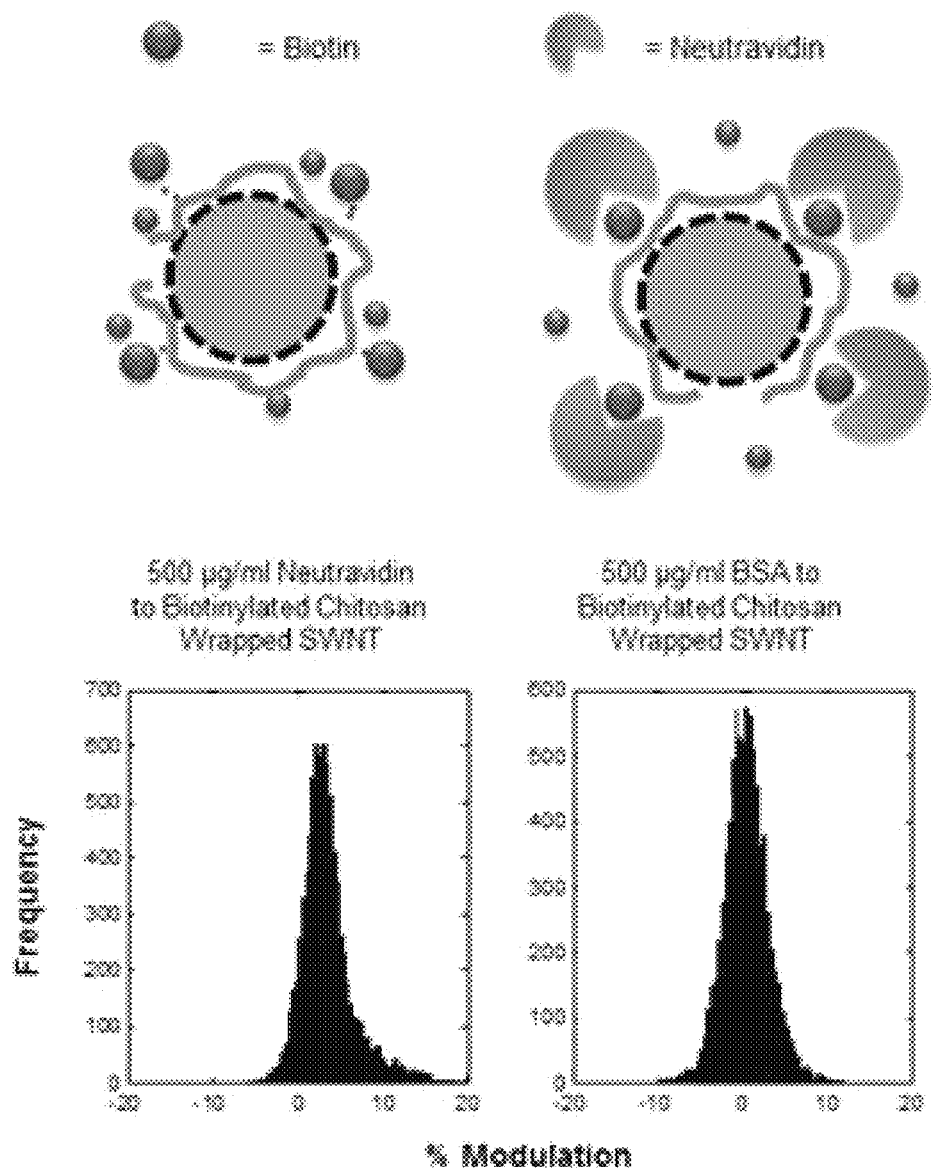
FIG. 2A illustrates the role of nickel in SWNT sensor modulation. Nickel was replaced with another small molecule binding site—biotin. Histograms show sensor responses of the biotinylated chitosan-wrapped SWNT to nuetravidin and BSA.
Figure 2B:
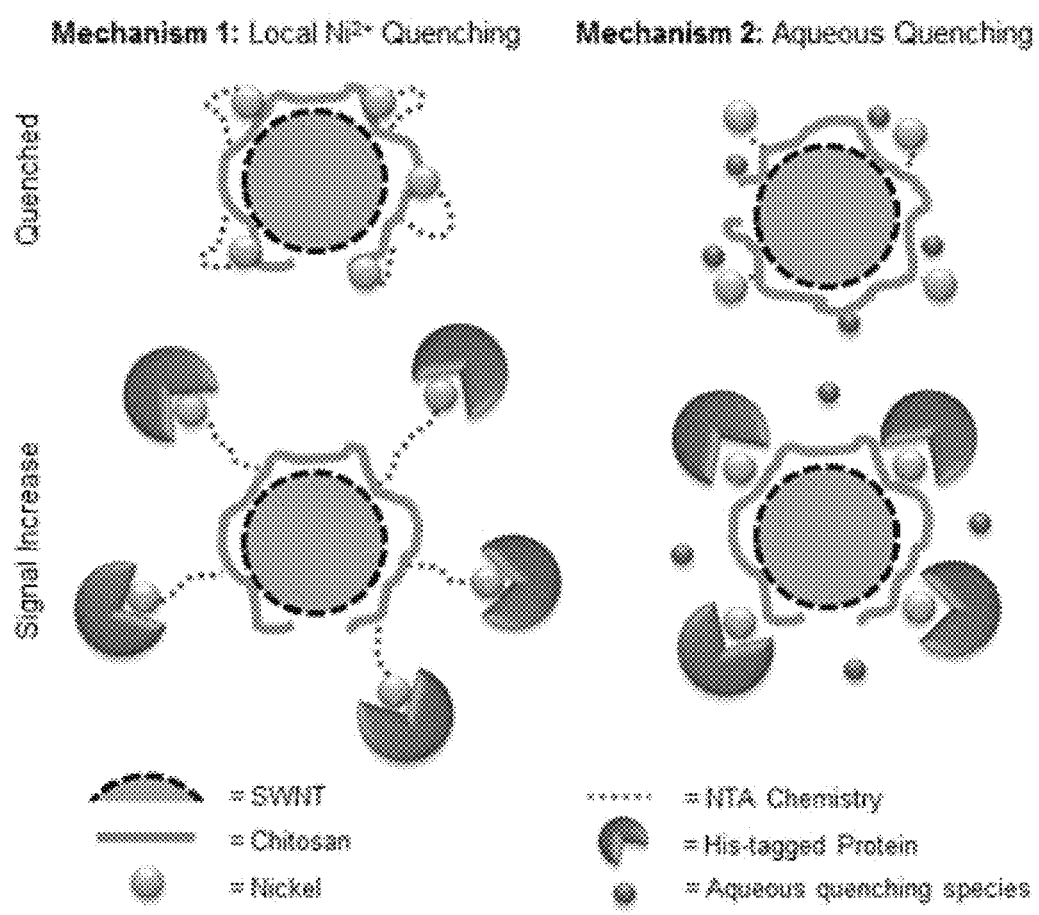
FIG. 2B illustrates two proposed quenching mechanisms at work. In Mechanism 1, the nickel acts as a quencher providing electronic states for non-radiative decay of the SWNT exciton. In Mechanism 2, the bound macromolecule displaces aqueous quenching species such as nickel and water from the SWNT surface.

It has been suggested that the chelated nickel used to bind the His-tag sensor protein is responsible for the modulation of the SWNT fluorescence. It is now clear that nickel quenches chitosan-wrapped SWNT in solution and immobilized on a surface (FIG. 1D). Divalent nickel cations have been shown to quench anionic surfactant wrapped SWNT and quantum dots (Brege, J. J., Gallaway, C. & Barron, A. R *Journal of Physical Chemistry C* 113, 4270-4276 (2009); and Wu, P. & Yan, X. P. *Biosensors & Bioelectronics* 26, 485-490 (2010); each of which is incorporated by reference in its entirety). The proximity of the chelated nickel groups altered the local electronic environment and offered non-radiative decay pathways for the SWNT exciton. To explore if this as the only mechanism at work, the nickel was replaced with another small molecule proxy—biotin. The chitosan wrapped SWNT were biotinylated with a commercially available NHS linker (Pierce) and then exposed to nuetravidin and a BSA control (500 μg/ml). The specific response was again a positive modulation and the control was null (FIG. 2A) although the turn on response was approximately 10% of what was typically seen when nickel was present. This result supports two interoperating mechanisms (FIG. 2B): (1) the sensor proteins were originally quenched by chelated nickel groups and the return of signal occurs when the nickel was displaced upon binding of the sensor protein or IgG, and (2) the chitosan wrapped SWNT was originally quenched by aqueous quenching species (water molecules, dissolved oxygen and protons have all been shown to quench exposed portions of suspended SWNT; see Strano, M. S. et al. *J. Nanoscience and Nanotechnology* 3, 81-86 (2003); and Blackburn, J. L. et al. *Nano Letters* 8, 1047-1054 (2008), each of which is incorporated by reference in its entirety) and the bound macromolecule displaced these species to cause a return in signal. A macroscopic swelling mechanism (as with PVA hydrogels, Barone, P. W. et al. *Acs Nano* 3, 3869-3877 (2009), which is incorporated by reference in its entirety) was ruled out, as the recorded movies of SWNT arrays during testing show that the SWNT sensors were indeed immobilized and did not move on the pixel resolution recorded (1.2 μm per pixel).

Response of Lyophilized Commercial Human IgG

Figure 3A:
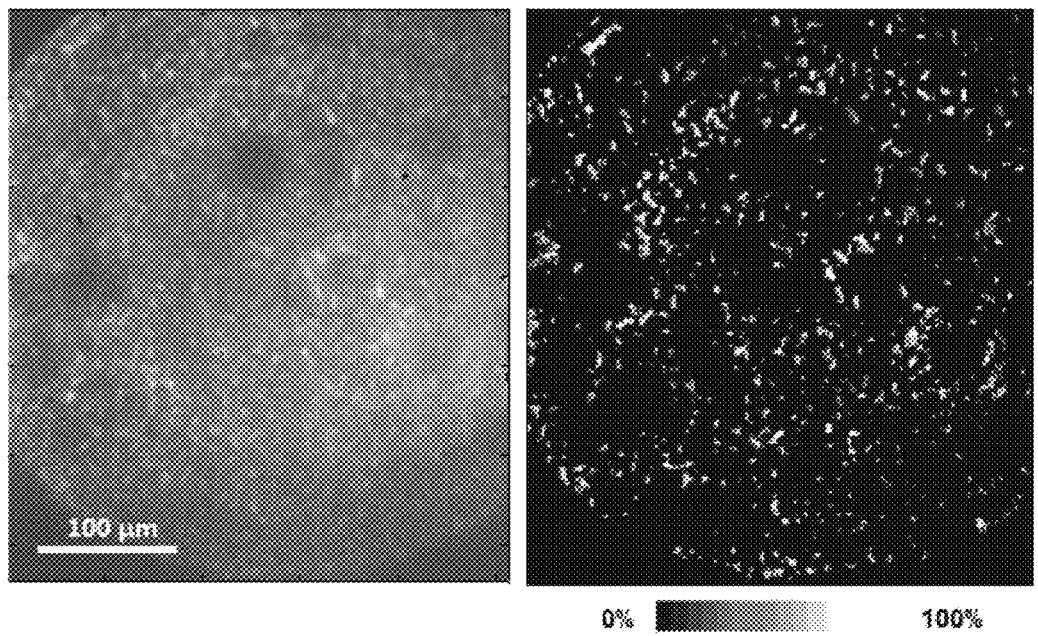
FIG. 3A shows and image and a heat map illustrating sensor response to lyophilized, commercial, polyclonal human IgG reconstituted in PBS at 1 mg/ml.
Figure 3B:
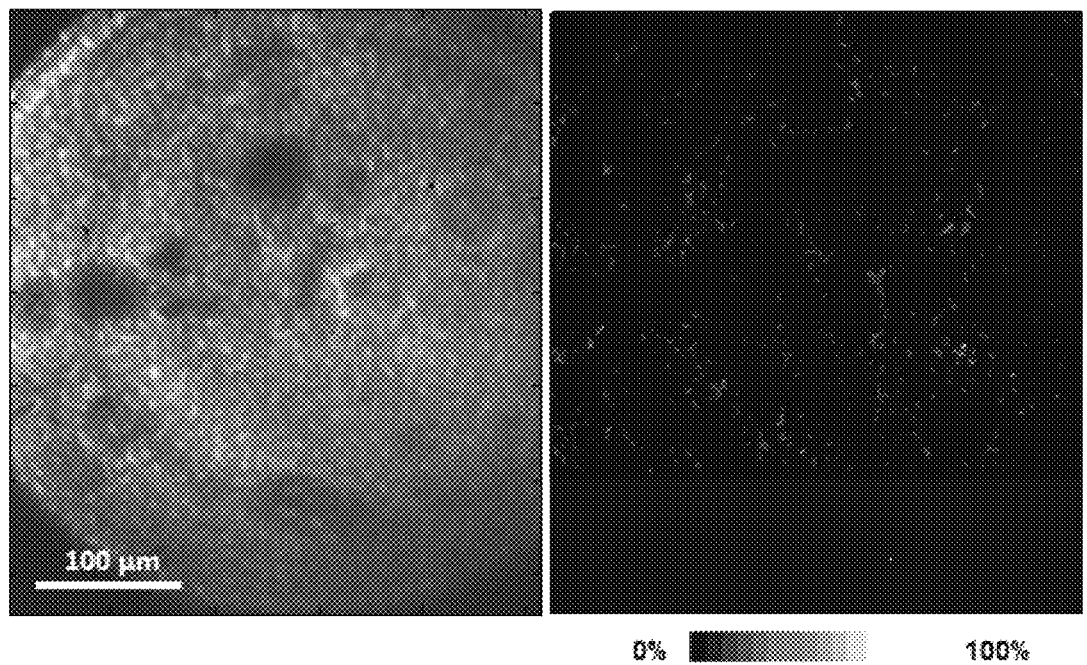
FIG. 3B shows and image and a heat map illustrating sensor response to BSA.
Figure 3C:
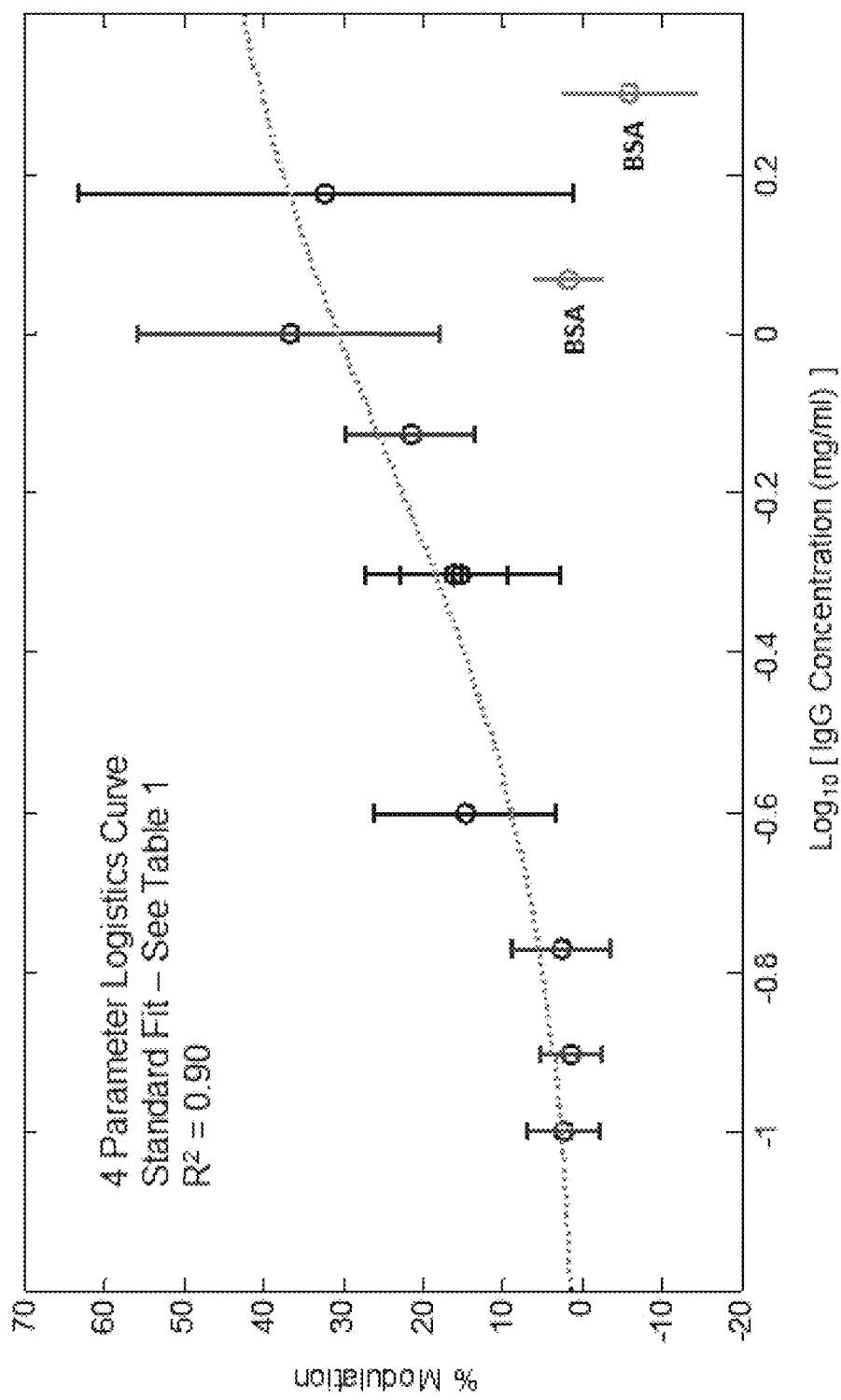
FIG. 3C is a graph showing a calibration curve for IgG. Sensor response for BSA is also shown.
Figure 3D:
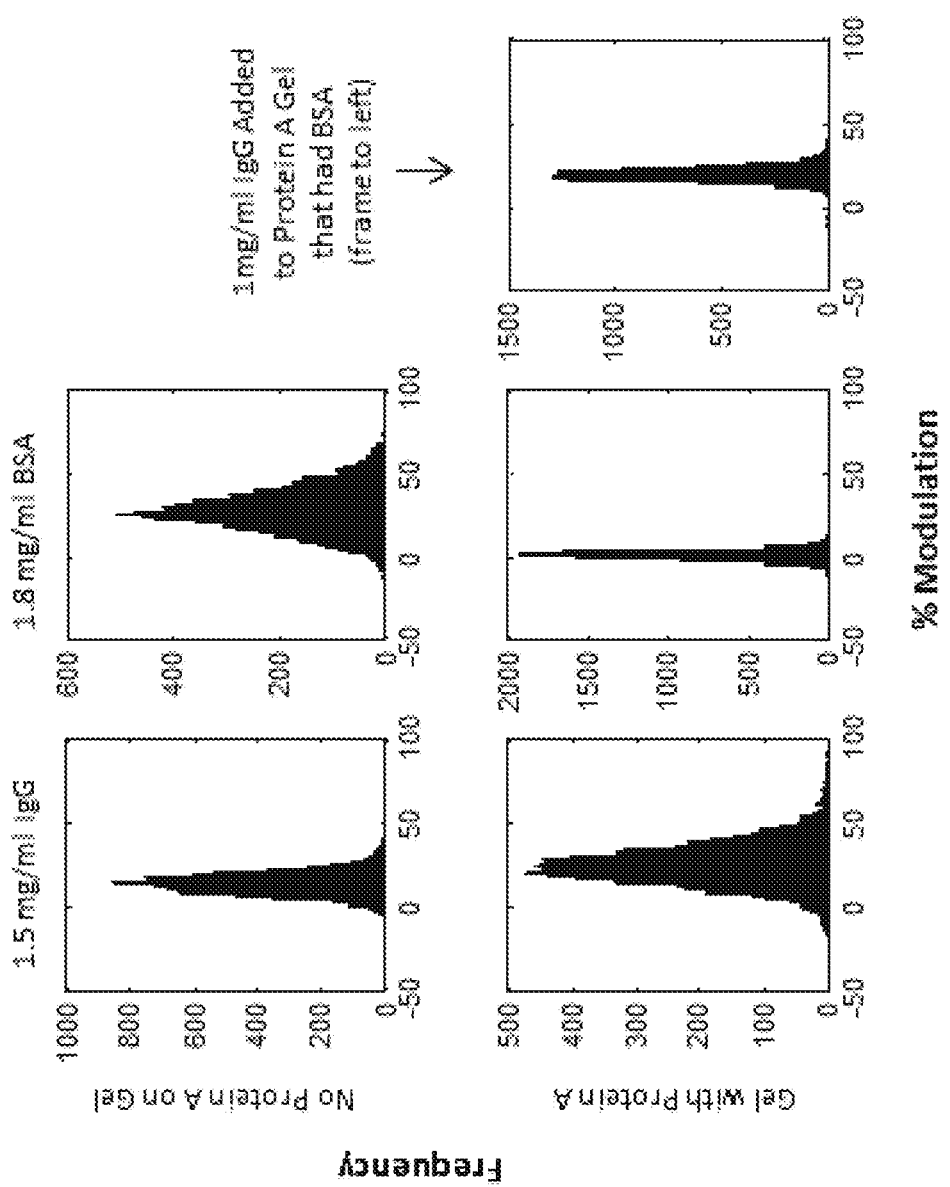
FIG. 3D shows sensor protein presence effect on nonspecific binding, data presented as distribution of all SWNT sensor sites.

After casting the gel, completing the chemical functionalization, and incubating with His-tagged protein A, the sensor platform was tested with commercial, lyophilized Human IgG (Pierce 31154) reconstituted in PBS. Selectivity was determined by using an equal or higher concentration of BSA and was reported as the difference in specific and nonspecific modulation, normalized by the minimum signal threshold (Table 1). The minimum signal threshold was calculated by first determining the variance in the baseline trace (standard deviation) and using a common heuristic that defines a significant signal as one being three times the value of the baseline variance (Table 1). Sensor response heat maps to IgG (FIG. 3A) and BSA (FIG. 3B) additions at 1 mg/ml revealed much higher modulation to the specific analyte. A calibration curve for IgG was created for this batch of gels (FIG. 3C) and was fit by a four parameter logistic curve, the standard for ELISA measurements. The fit ($R^2=0.90$) also provided the limit of detection by assuming that the response must be above the minimum signal threshold. For the lyophilized product, the minimum detection limit was 1.4 μg/ml with a high saturation value—likely due to the inefficient binding of the lyophilized product as compared to freshly expressed product (discussed below). Additionally, a set of control experiments showed that the docked sensor protein (Protein A) was needed to render the gel specific (FIG. 3D).

TABLE 1

| | Saturation Signal | Saturation (95% of Max) | Minumum Signal Threshold (3*σ-Noise) | Minimum Detection Limit | Selectivity: $(\mu_{Specific}-\mu_{Non-specific})$/ Signal Threshold |
|---|---|---|---|---|---|
| Lyophilized Human IgG in PBS on Protein A: | 49% | 200 g/ml | 4.7% | 1400 ng/ml | 7.5 |
| Murine IgG from HEK Supernatent on Protein A: | 50%* | 8.3 mg/ml | 3.1% | 70 ng/ml | 5.2 |
| Human IgG from CHO Supernatent on Protein A: | 48% | ~630 ng/ml | 8.3% | — | — |
| Chicken IgG on PSA Lectin: | 54% | ~1 mg/ml | 5.8% | — | 10.5 |
| Hypermannosylated IgG from CHO on PSA Lectin: | 50%* | ~100 ng/ml | 3.5% | ~2 ng/ml | 7.5 |

*Upper threshold not attained-value essumed from other screening.

4 Parameter Logistics Curve Parameters-ELISA Standard Fit

| | A | B | C | D | $R^2$ Fit |
|---|---|---|---|---|---|
| Lyophilized Human IgG in PBS: | 0.00 | 1.47 | 0.71 | 0.49 | 0.90 |
| Murine IgG from HEK Supernatant: | -0.05 | 4.46 | 3.50 | 0.50 | 0.99 |
| Human IgG from CHO Supernatant: | 0.09 | 59.40 | 2.67 | 0.48 | 1.0† |

†Only 4 days of culture were attained and assayed-thus the "perfect" fit should not be used to predict minimum detection limit.

Response of Cell Culture Supernatant: HEK, CHO, and Commercial Fungal System

Figure 4A:
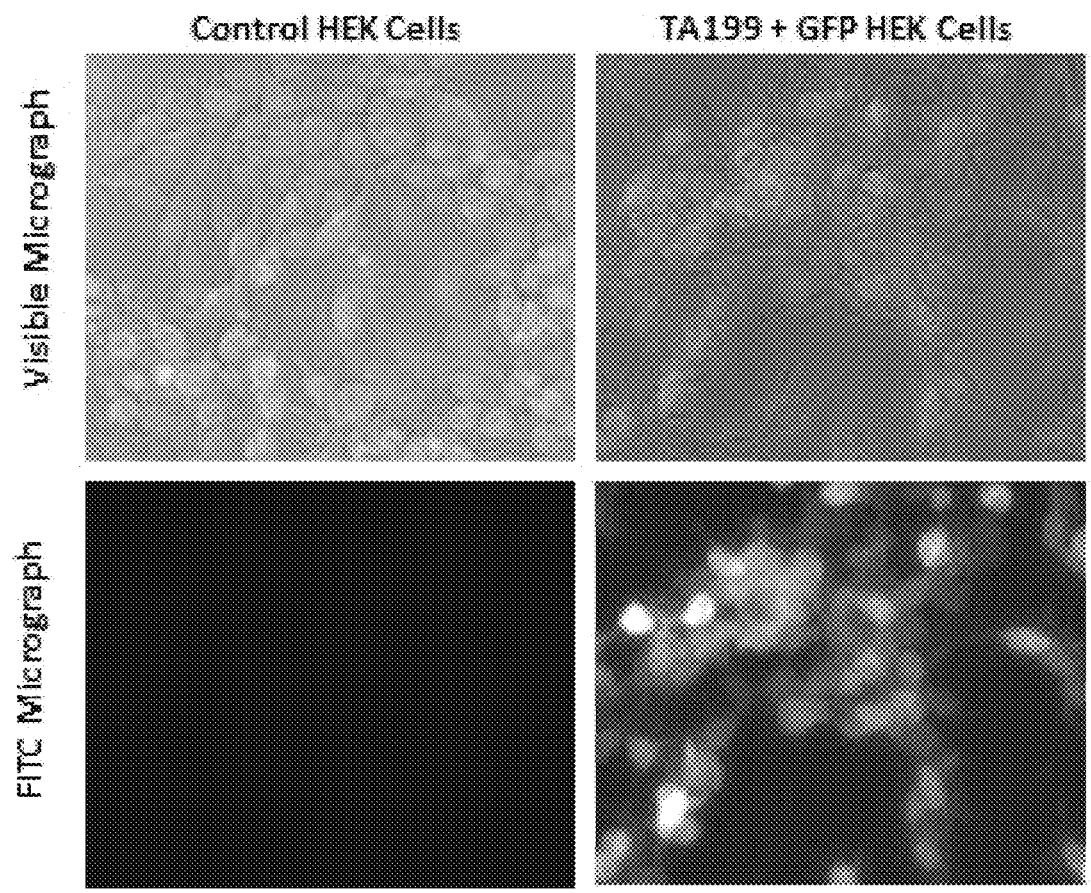
FIGS. 4A-4D show results of cell culture extract supernatant studies.
Figure 4B:
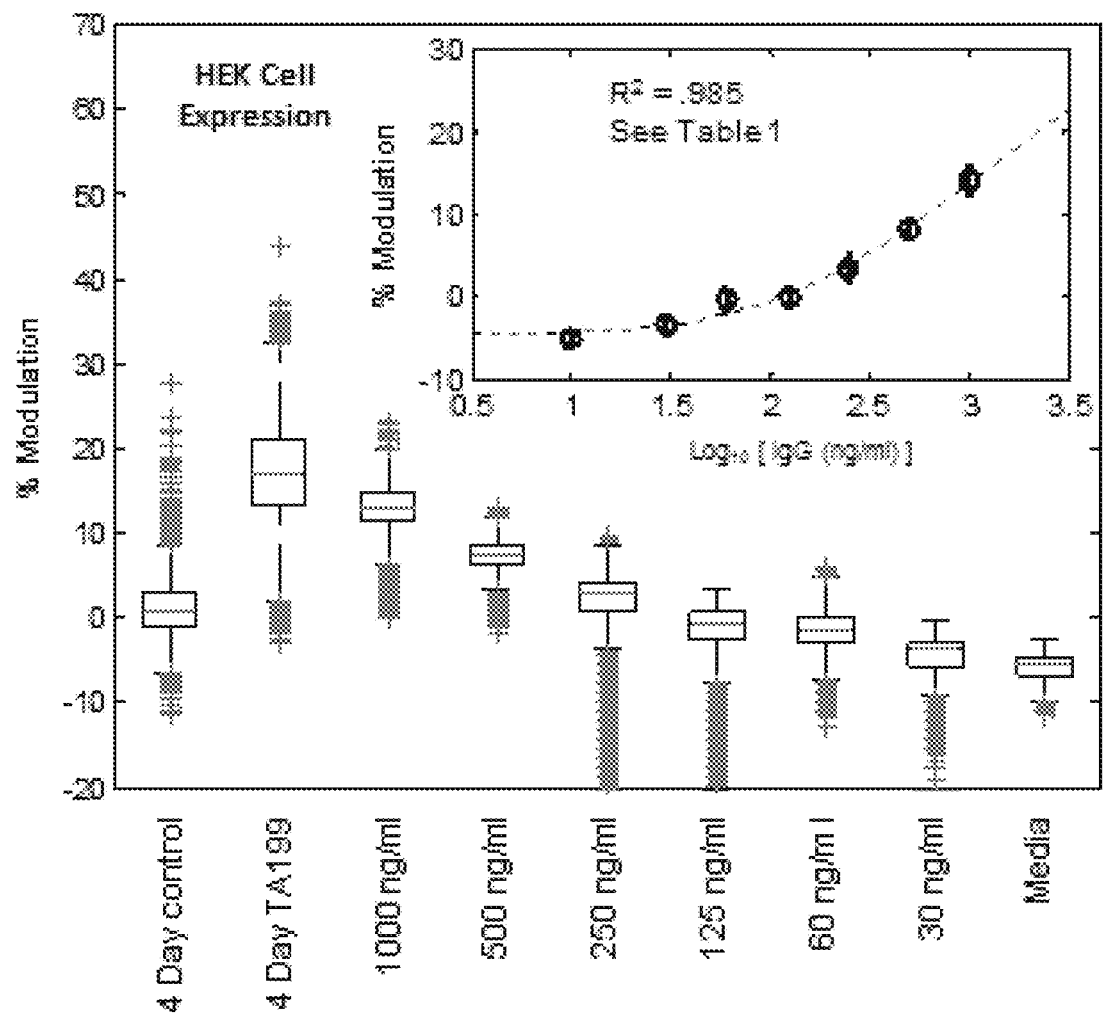
Figure 4C:
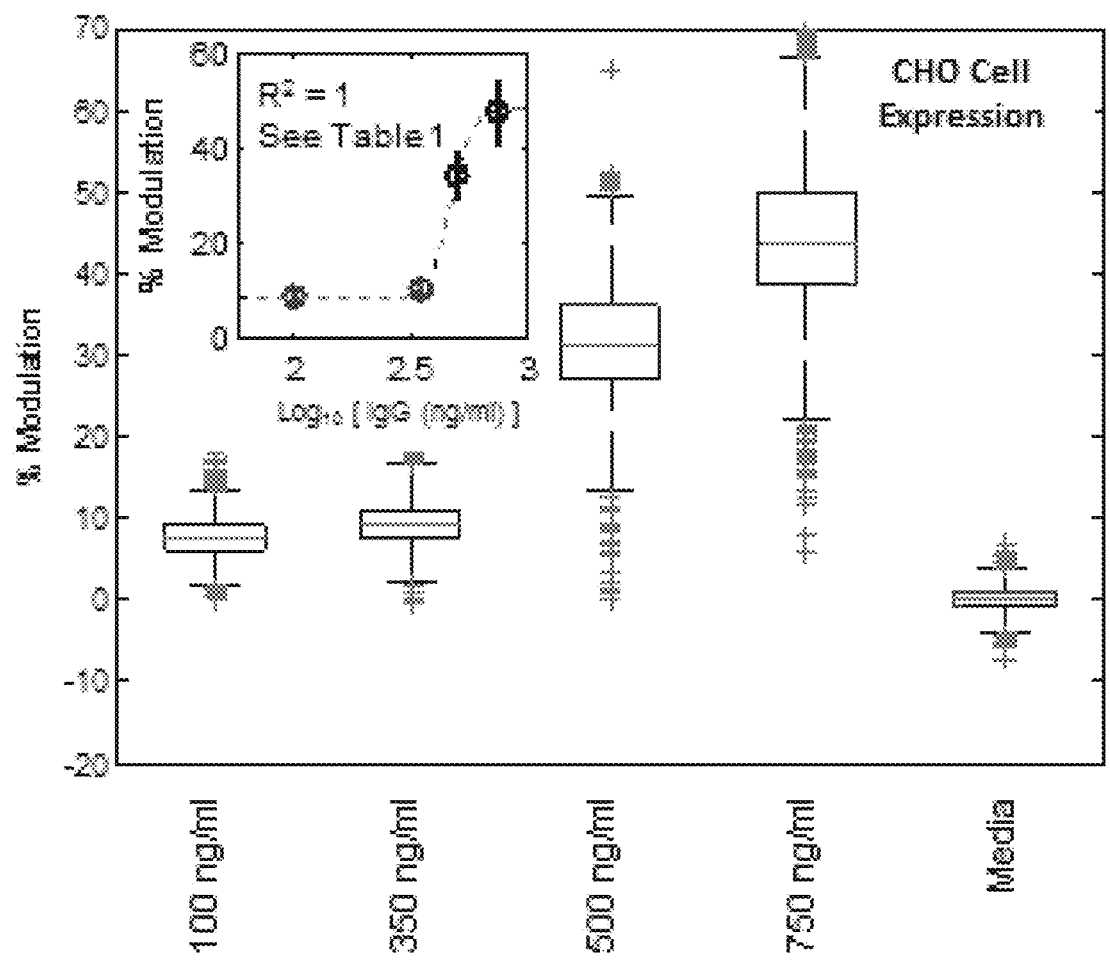

A human embryonic kidney (HEK) hybridoma cell line was transfected to produce both GFP and a murine IgG (TA99). This provided a convenient control, as the non-transfected cells could be visually inspected with a FITC filter to confirm the absence of a GFP signal (FIG. 4A). First, the control HEK cells and TA99 producing HEK cells were seeded at equal density and grown for four days in serum-free media (Invitrogen Freestyle 293). The cell extract supernatants of both were then screened, showing a statistically significant increase in signal for the antibody producing cells (FIG. 4B) and good selectivity (Table 1). Another culture of TA99 HEK cells was grown four days and the cell extract supernatant was assayed at different dilutions (FIG. 4B), which provided a calibration curve for this cell line (traditional ELISA was used to assay the antibody concentration). Again the fit was tight ($R^2=0.99$) and the minimum detection limit was 20 times lower than the commercial lyophilized product (Table 1). The expression media was also screened, showing no appreciable signal increase.

Figure 4D:
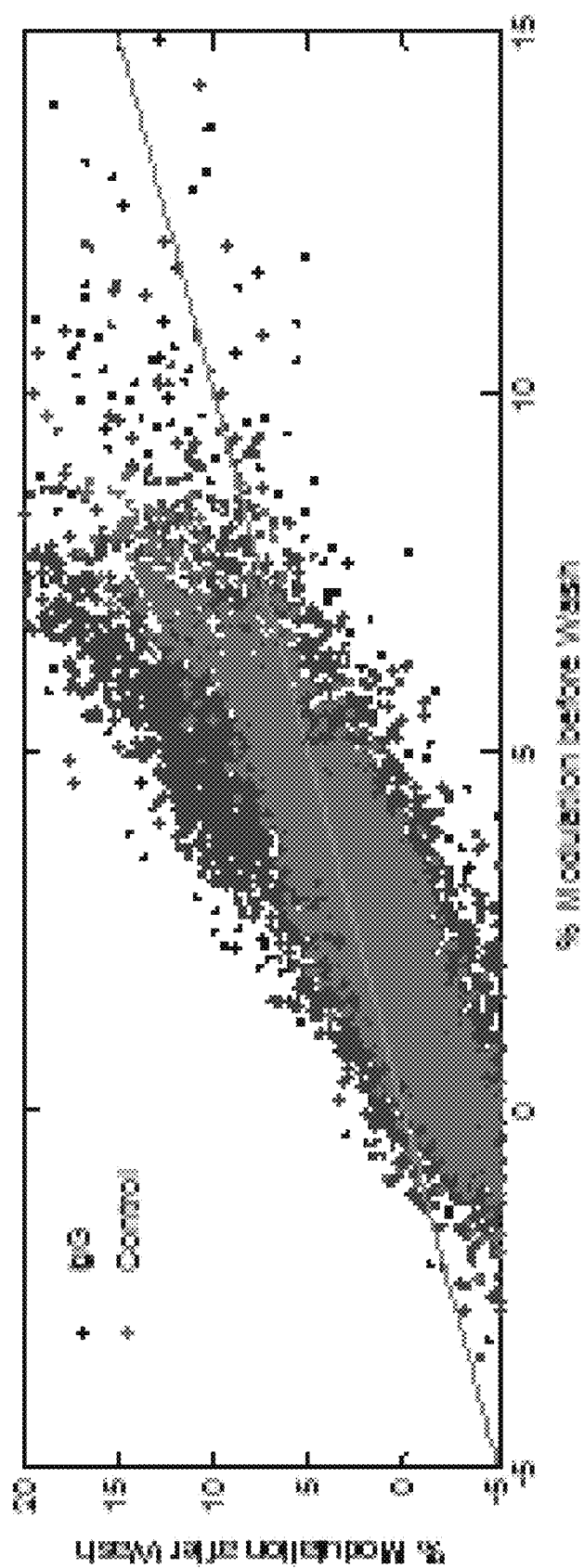

Human IgG (b12)-producing Chinese hamster ovary (CHO) cells were also tested. Again, a confluent monolayer of CHO cells were cultured in serum free growth media and samples were taken for four days every 24 hours; the resulting signal response matched the expected growth pattern (FIG. 3C). Concentrations of the samples were determined with traditional ELISA; the number of samples were not sufficient to determine a minimum detection limit for this culture. However, saturation of these sensors occurred at a much lower concentration (<1 ug/ml) than the other IgG types assayed. This was due to the high affinity of human IgG to protein A as opposed to murine IgG, and it being a freshly expressed product (i.e. no damage caused by lyophilization). Another method to distinguish between specific and unspecific reactions was to determine the response upon addition and then the remaining response after washing. At 10×, the IgG-containing sample had a higher retention rate (above the red line) than the control cell line (FIG. 4D).

Hypermannosylation Study—Chicken IgG, CHO Cultures, and Rituximab Standards

Figure 5A:
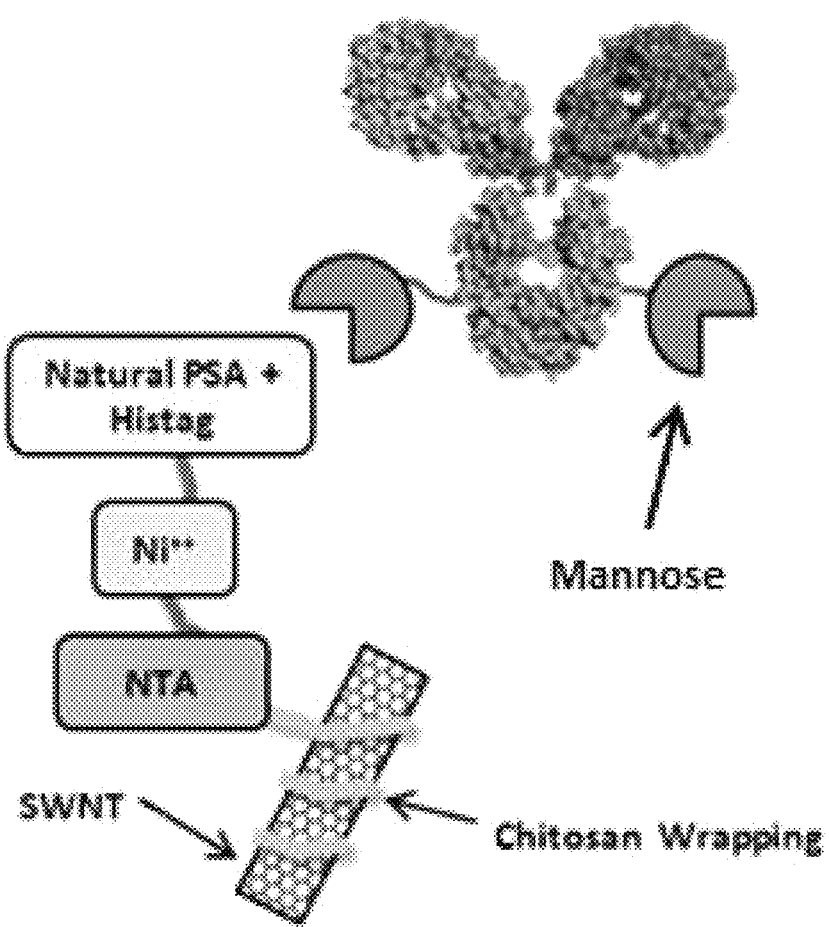
FIG. 5A illustrates a photoluminescent nanosensor construct rendered specific to mannose by docking a chemically His-tagged PSA lectin to a SWNT.
Figure 5B:
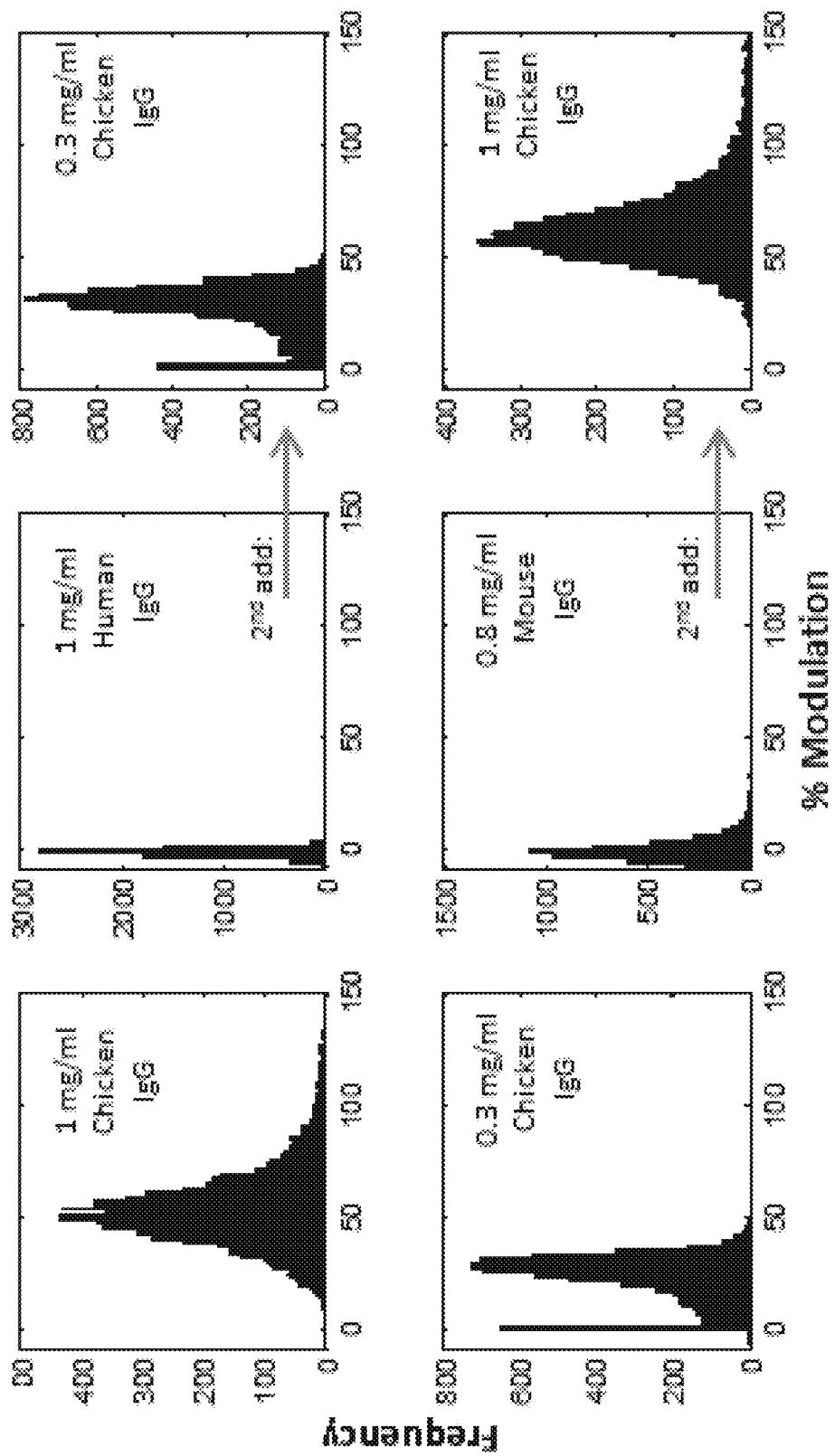
FIG. 5B shows sensor response validated with varying species of IgG—chicken IgG contains a higher percentage of high-mannose glycoforms whereas these are not present in human and mouse IgG.

With a His-tagged, mannose-specific plant lectin, *Pisum sativum* agglutinin (PSA) the sensor platform can be rendered specific to high mannose content species (FIG. 5A). Different species of IgG were used to test this concept. It has been shown that Chicken IgG contains an appreciable amount of high mannose content glycoforms (>40% of population) whereas these are virtually absent in human and mouse IgG (see Raju, T. S., et al. *Glycobiology* 10, 477-486 (2000), which is incorporated by reference in its entirety). The SWNT sensor responses to human, mouse, and chicken IgG in PBS aligned with these findings and confirmed that the platform can be rendered specific to mannose species with the PSA lectin (FIG. 5B).

Figure 5C:
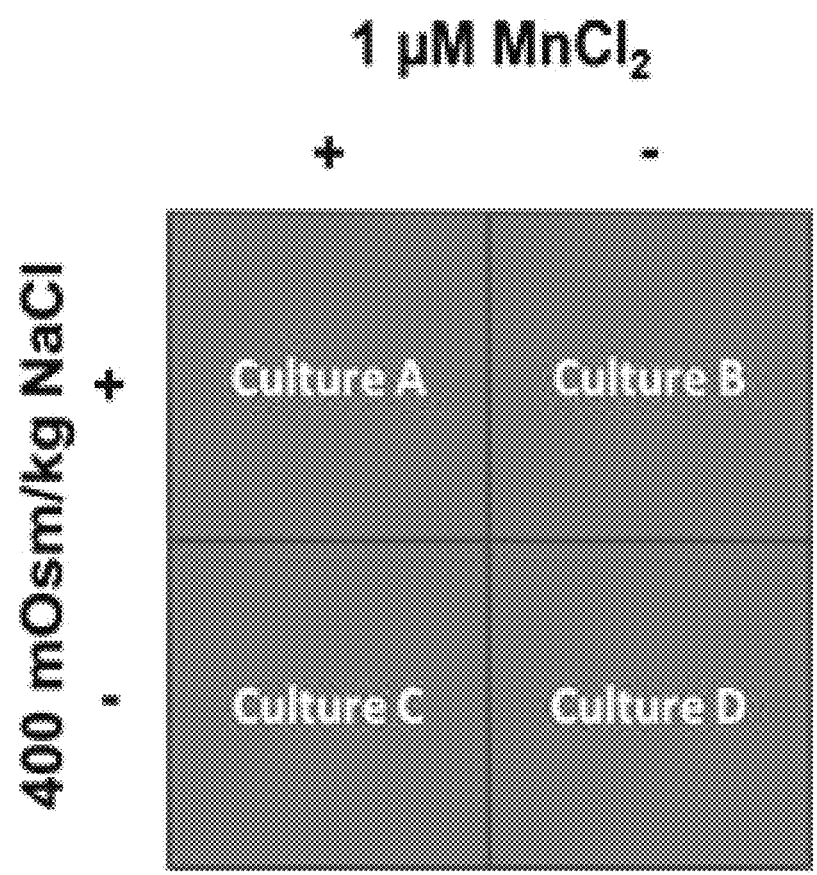
FIG. 5C shows the experimental design for four cultures grown in parallel while feeding different media to induce changes in hypermannosylation.
Figure 5D:
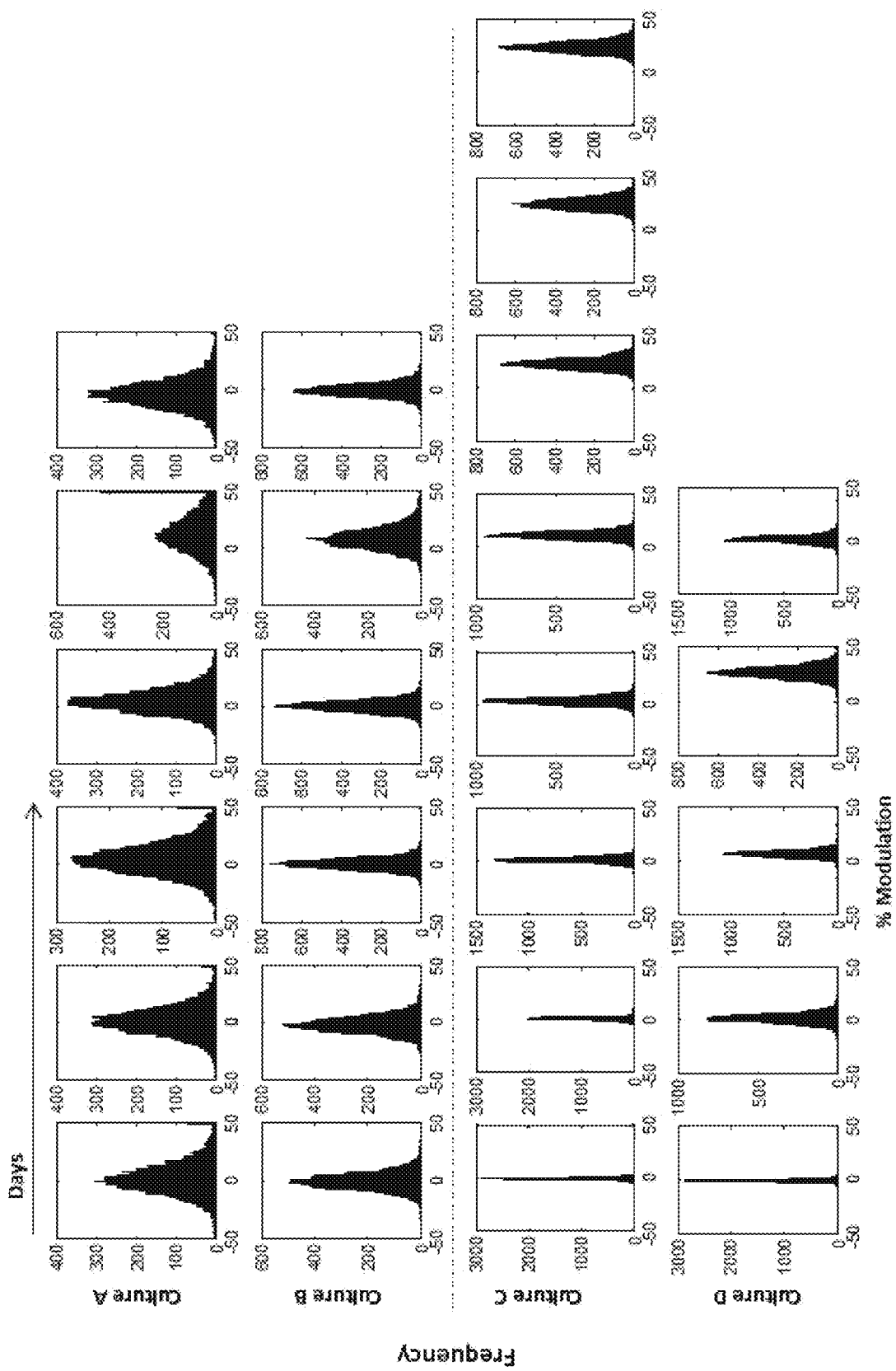
FIG. 5D shows raw trends in mannosylation of each 24 hr period diluted to 10 ng/ml presented as distributions of all SWNT modulation.
Figure 5E:
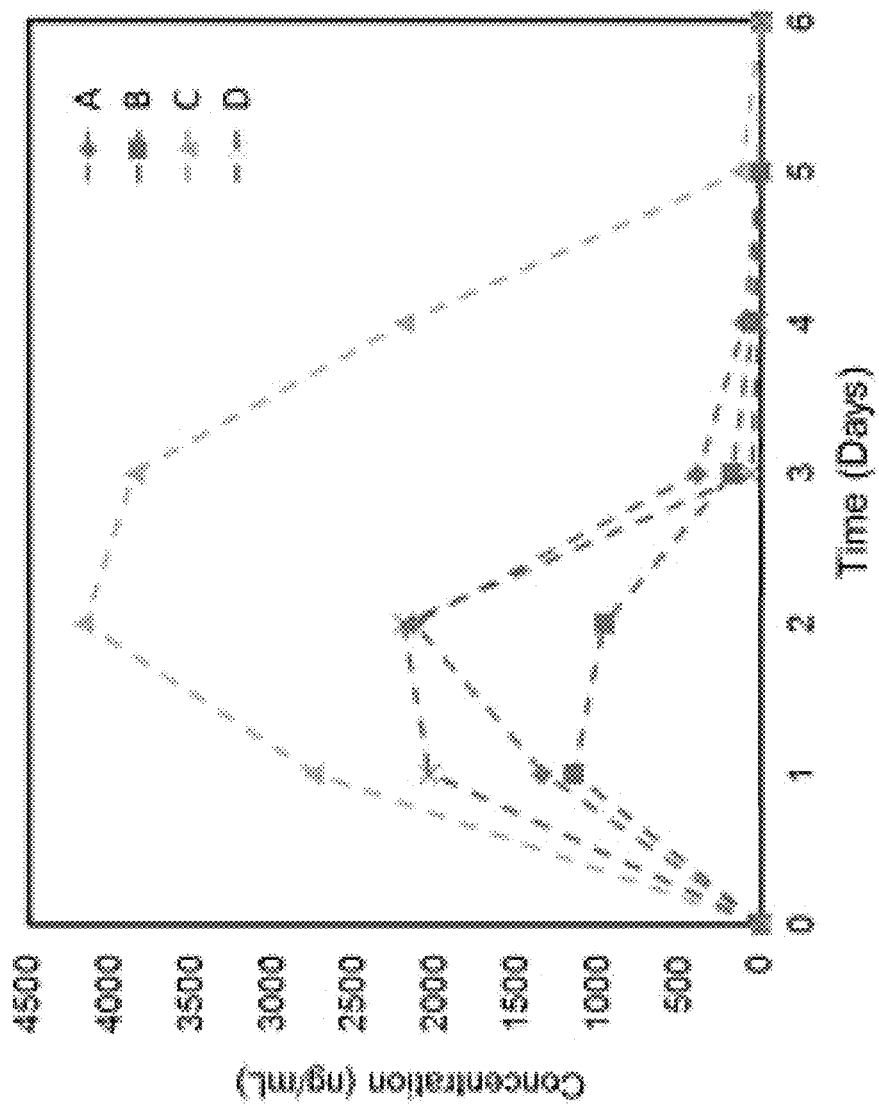
FIG. 5E shows IgG titer for each of the culture days.
Figure 5F:
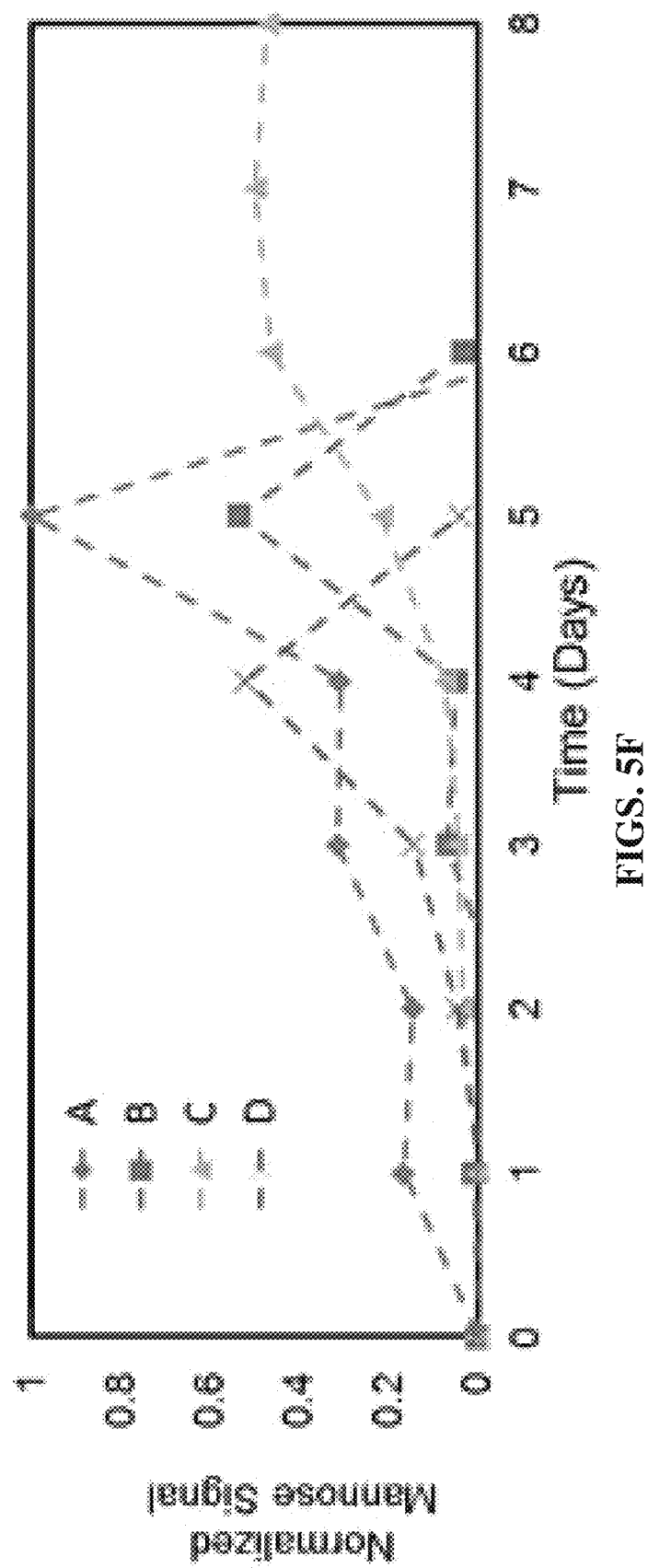
FIG. 5F shows general trends of mannosylation derived from the distribution averages in FIG. 5D.

Changing culture conditions (e.g., media composition) can affect the onset and extent of IgG hypermannosylation. In order to further validate our platform, levels of NaCl were increased and a $MnCl_2$ additive was used with CHO cultures while monitoring mannose content over time using traditional Peptide-N-Glycosidase F release and capillary electrophoresis. See Pacis, E., et al. *Biotechnology and Bioengineering* 108, 2348-2358 (2011), which is incorporated by reference in its entirety. Four identical dishes of CHO cells were cultured and fed media compositions derived from this study (FIG. 5C). The cell extract supernatant was collected after each 24 hour period, diluted to a standardized 10 ng/ml IgG concentration, and assayed on PSA rendered sensor gels (FIG. 5D). The IgG concentrations were determined with ELISA (FIG. 5E) and if below 10 ng/ml, the sample was run at stock concentration. The resulting trends (FIG. 5F) matched those found in the previous study: 1) increased mannose content as culture time increased, 2) increased mannose from higher NaCl osmolality, and 3) delayed onset of hypermannosylation from $MnCl_2$ additive. The presence of mannose in these samples was confirmed by surface staining with fluorescently tagged PSA but the sensitivity of existing glycan analysis techniques was inadequate to confirm the trends measured on these low concentration samples.

Local Cell Colony Production

Figure 6A:
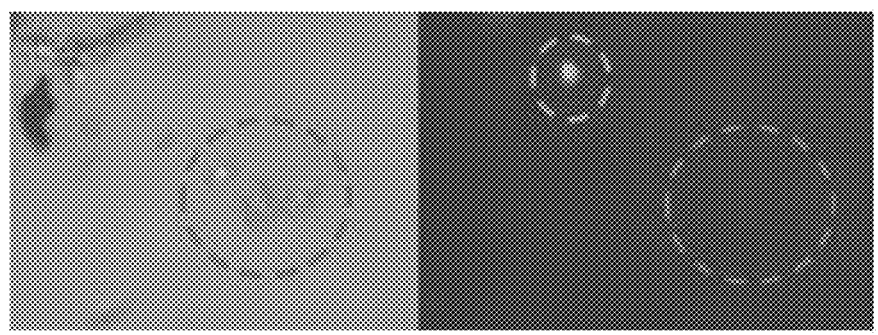
FIGS. 6A-6E illustrate sensor response to local cell production.
Figure 6A:
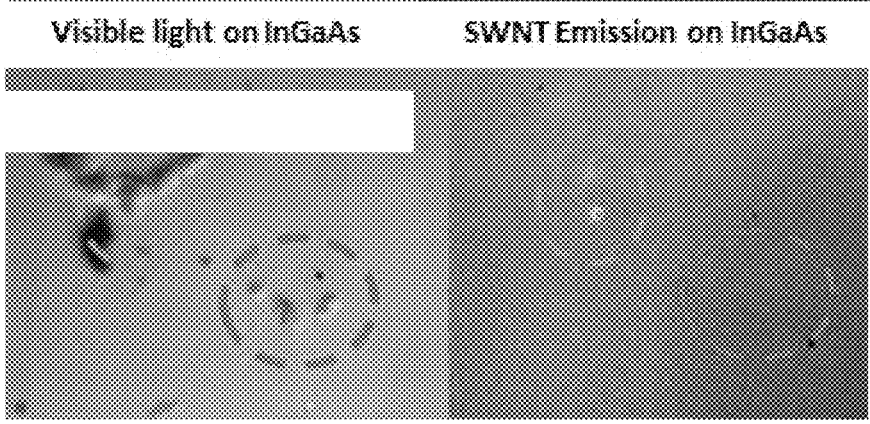
Figure 6B:
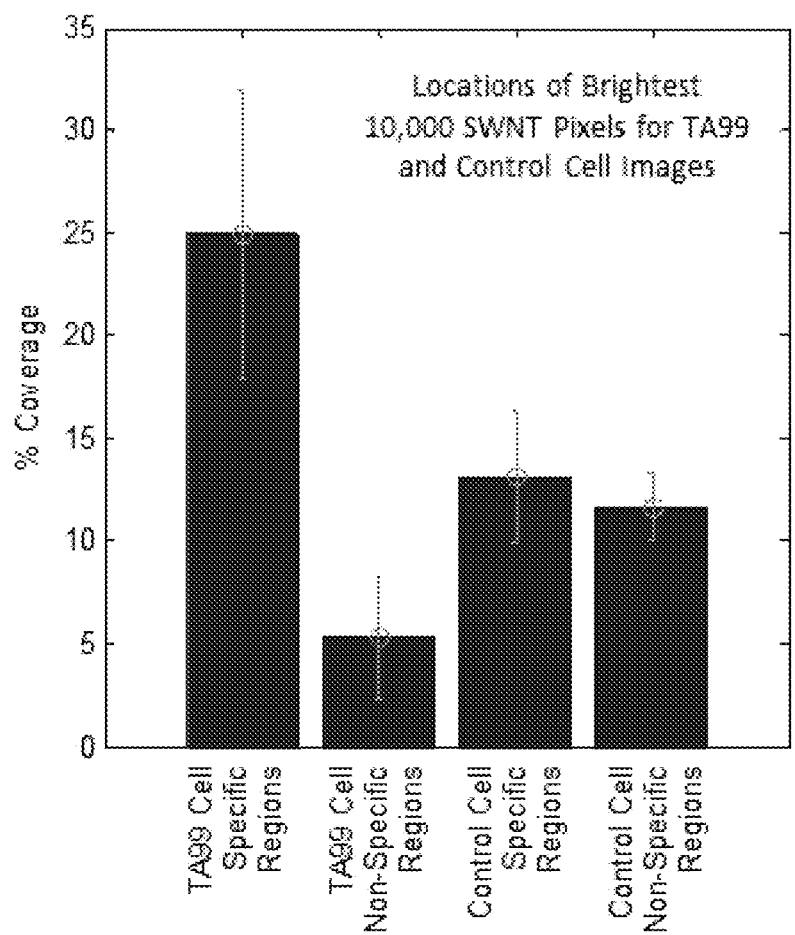
Figure 6C:
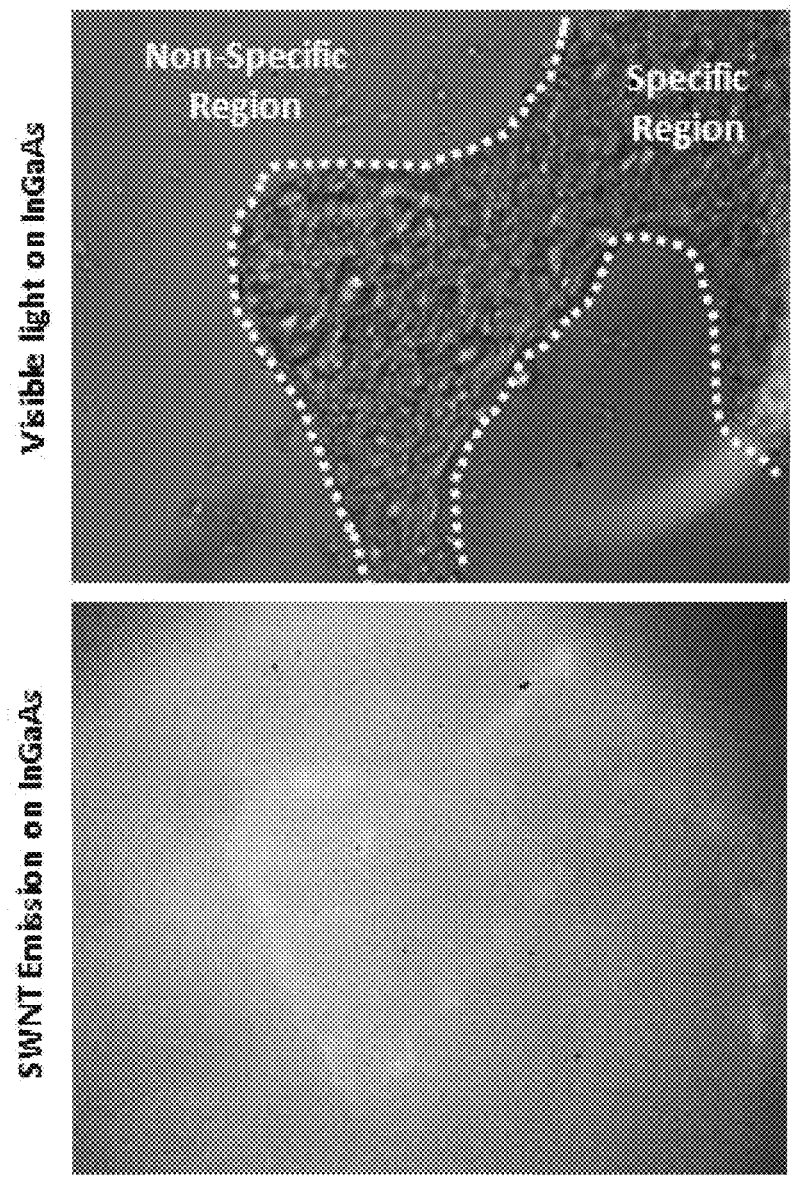
Figure 6D:
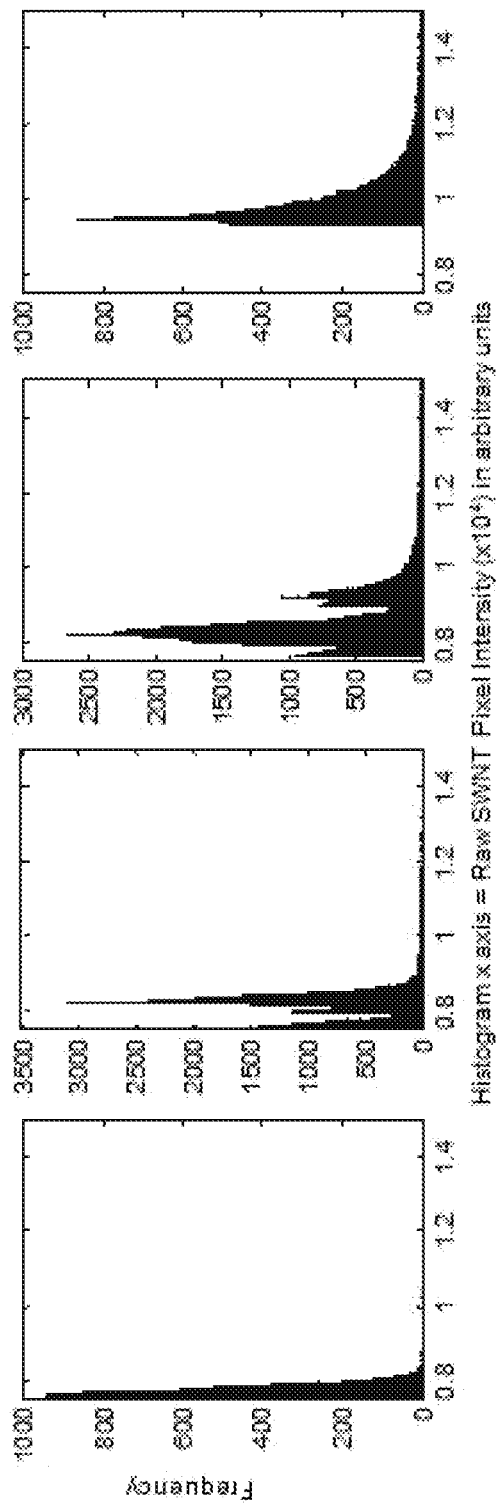
Figure 6D:
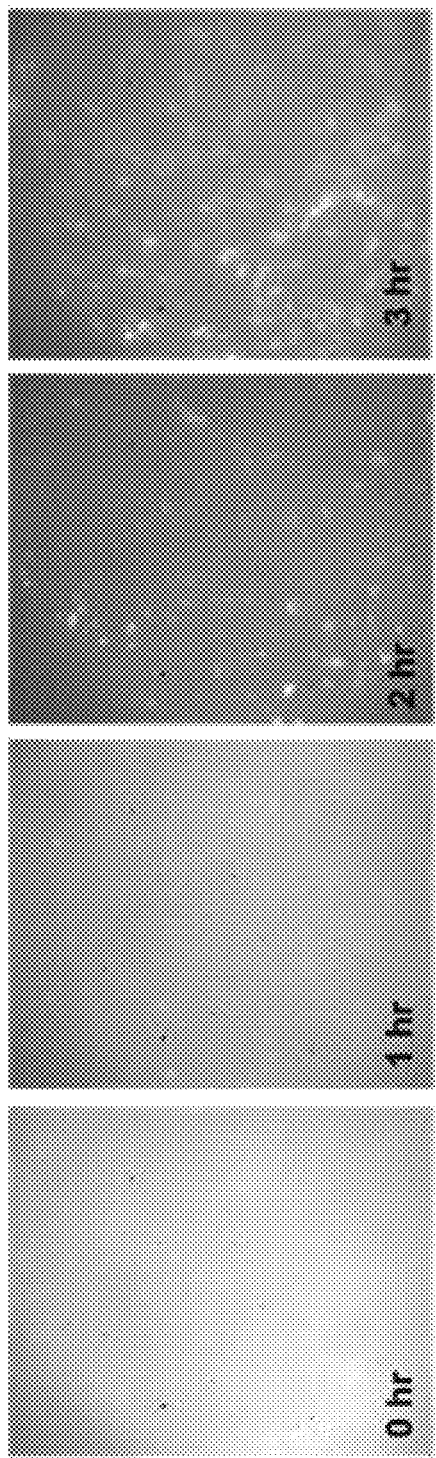
Figure 6E:
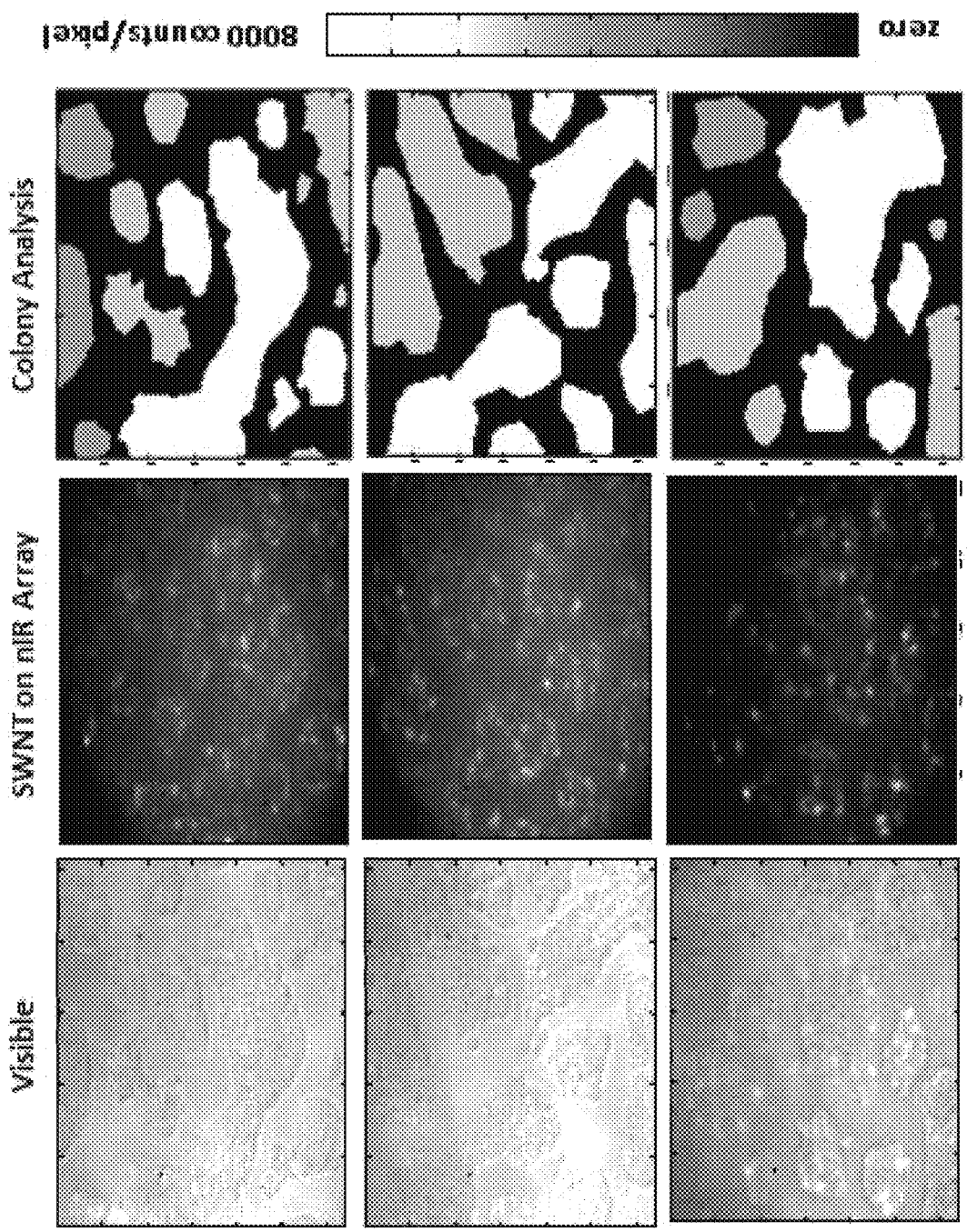

A gel with imbedded nanosensors can be used to screen local production of cells. Single cells can be difficult to culture for long periods of time on the porous hydrogels (little indications of healthy, single cell adherence). Some single cells were cultured qualitatively and, displayed colocalization of IgG production on a Protein A-incubated gel (FIG. 6A). By seeding a greater number of cells, larger cell colony islands formed on the porous gel surface which were able to produce for longer time periods. By analyzing images of control and IgG producing HEK cell islands after 24 hours of production, a statistical difference between the two production profiles was seen. By ranking the brightest 1000 SWNT and then querying their location, there was a greater localization of the bright SWNT under IgG producing islands whereas they were evenly or randomly distributed within and outside of the control cell islands (FIGS. 6B-6C). HEK producing cell islands were plated on a gel, then multiple images of the nIR intensities at 0, 1, 2, and 3 hours were acquired. Histograms of the 1000 brightest SWNT pixels in these images showed a 'turn-on' trend that was likely due to IgG production (FIG. 6D). Finally, large HEK islands were allowed to grow overnight on a Protein A gel. The nIR response was clearly co-localized under each of the islands, and the response was summed and averaged over the island area and each island was ranked based on productivity (FIG. 6E).

Characterization of the Polyacrylamide Network

Figure 7A:
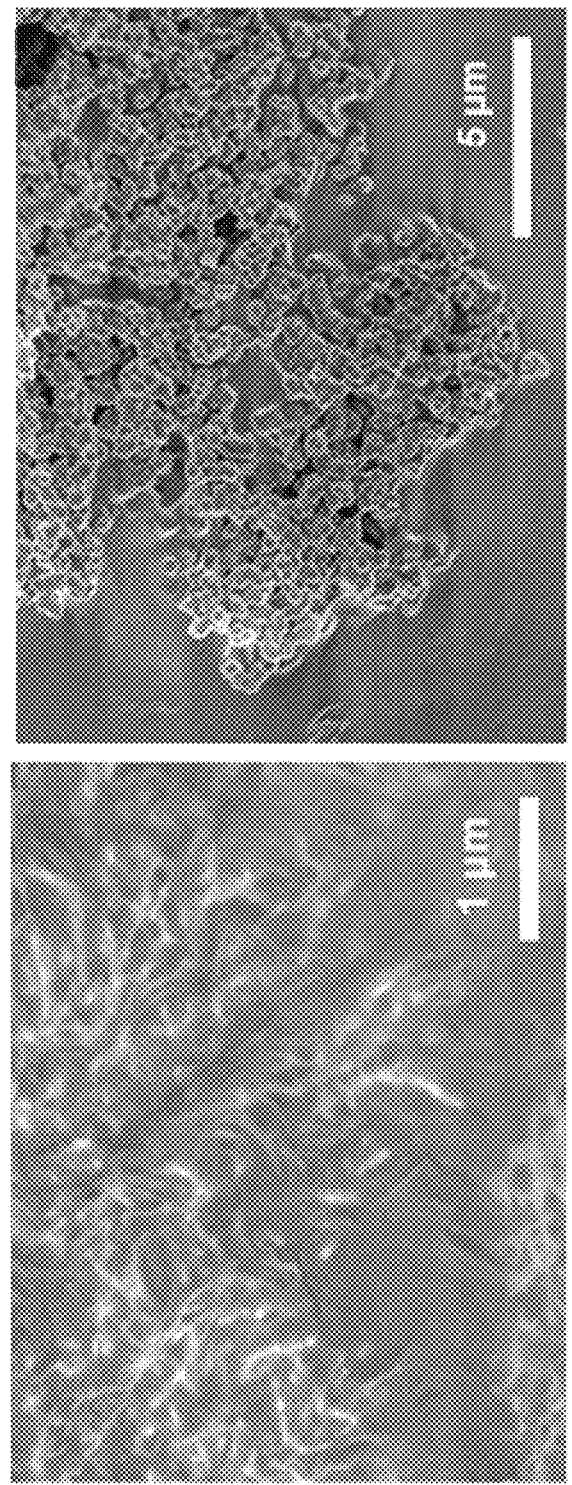
FIGS. 7A-7D. Characterization of the polyacrylamide sensor gel network.

The thin, top polyacrylamide gel entrapped the SWNT sensors in a sparsely crosslinked network. If the chitosan wrapped SWNT were added to the solution containing acrylamide monomers and bis-acrylamide crosslinker immediately, the resulting gel had a homogenously distributed SWNT pattern. Conversely if the SWNT were allowed to interact with the monomer and crosslinker solution during the bottom gel curing time, the amine groups on the chitosan-wrapped SWNT underwent linear step growth Michael Addition Polymerization with the bisacrylamide cross-linker (forming poly amido amines), leading to larger fluorescent SWNT clusters. The cluster sizes were dependent on the interaction time of these two constituents before starting the radical polymerization that consumed the remaining crosslinkers and immobilized the clusters. These clusters can be clearly seen in the nIR micrographs (FIG. 1C), raman maps, visible micrographs, SEM (FIG. 7A), and TEM imaging and were found to be more responsive to IgG than the gels with sparse, evenly distributed SWNT.

Figure 7B:
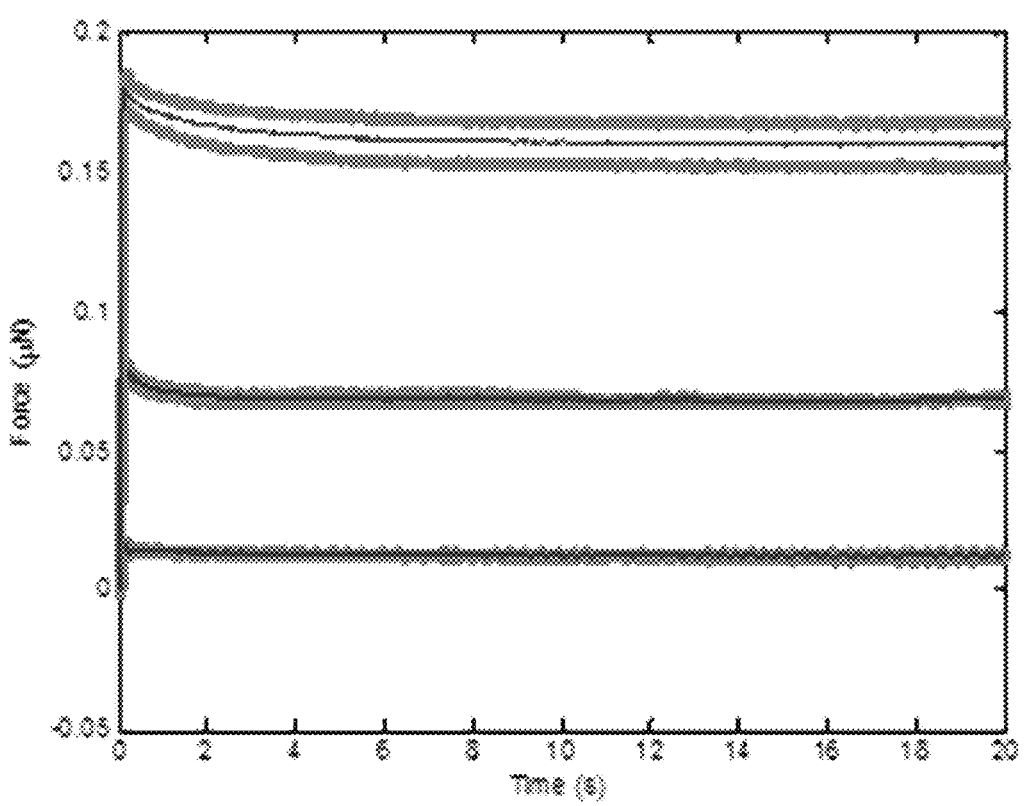
Figure 7C:
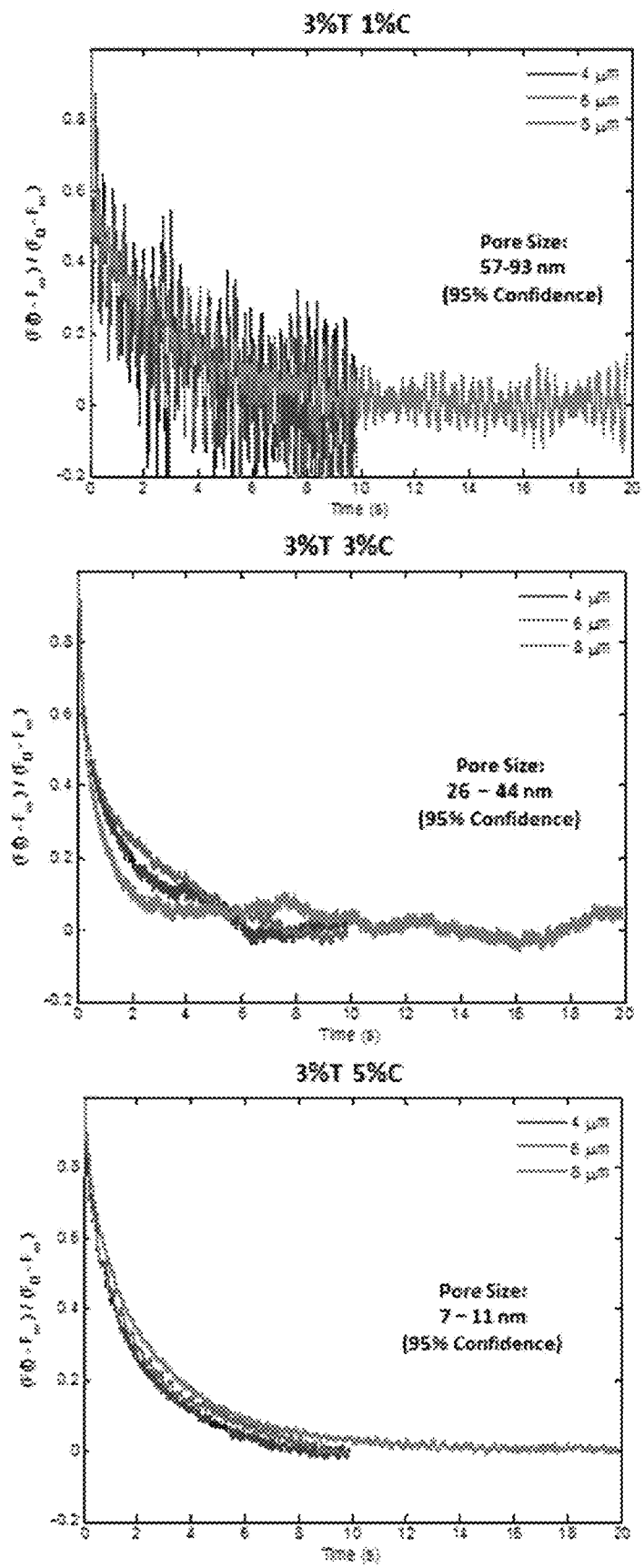
Figure 7D:
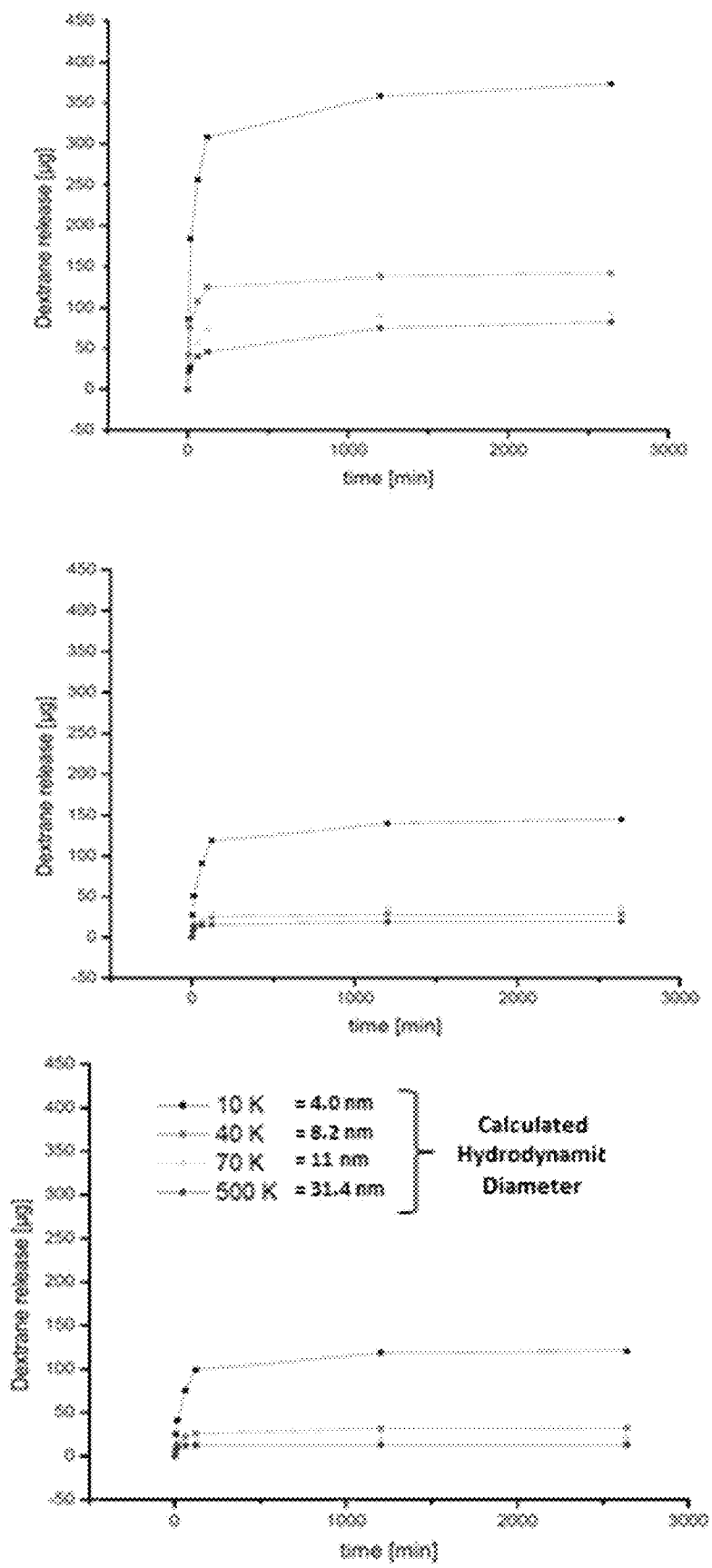

A top acrylamide gel layer containing the SWNT sensors was prepared with larger pore sizes. This was done by protecting the radical polymerization in a nitrogen-filled glove box from quenching oxygen species. Solutions with as low as 3 wt % polymer (97% water) were able to be crosslinked in this environment. The effect of crosslinker concentration on pore size has been established qualitatively in literature with TEM imaging (Ruchel, R., et al. *J. Chromatography* 166, 563-575 (1978), which is incorporated by reference in its entirety), but the pore size of these gels were determined experimentally to ensure that large antibodies could diffuse to the sensor sites. The pore size measurements were carried out with FITC dextran release profiles (FIG. 7D) showing that the largest dextran probe used (31.4 nm in diameter) was able to freely diffuse into the 3% T 1% C optimized gel (% C is standard nomenclature for the crosslinker weight percent of the total polymer weight percent (% T), thus in this case it would be 0.03 wt % of the total mixture).

The pore size was measured by microscale poroelastic indentation. See Kalcioglu, Z. I., et al. *Soft Matter* 8, 3393-3398 (2012), which is incorporated by reference in its entirety. In brief, a microsphere that was orders of magnitude larger than the average pore size (R=22.5 µm) was indented into the gel at a specified distance (h) and held while the displaced solvent leaked into surrounding regions. The resulting force versus time curve (FIG. 7B) exhibited an initial spike ($F_0$) that relates to the shear modulus of the gel (G in Eq 1) and then relaxed to an equilibrium state ($F\infty$) which relates to the diffusion constant of the displaced fluid. The force relaxation curve was obtained for multiple penetration depths (h=8, 6, and 4 μm), normalized (FIG. 7C) and fit by a numerically solved model for an indented sphere geometry to determine the diffusion constant (D in Eq 2) and Poisson ratio (v, in Eq 3) (Hu, Y. H., et al. Applied Physics Letters 96 (2010), which is incorporated by reference in its entirety). These parameters and the viscosity of water (q) were then used to solve for the average pore size of the network ($\xi_p$ in Eq 4) (see Chan, E. P., et al. *Soft Matter* 8, 1492-1498 (2012), which is incorporated by reference in its entirety). These measurements yielded an average pore size of 57-93 nm (95% confidence interval) which was 5-9 times the calculated size (~10-11 nm) of a hydrated IgG antibody (see Armstrong, J. K., et al. *Biophysical Journal* 87, 4259-4270 (2004), which is incorporated by reference in its entirety).

$$F_0 = \frac{16}{3} G (\sqrt{Rh}) h \quad \text{Eq. 1}$$

$$\frac{F(t) - F_\infty}{F_0 - F_\infty} = 0.491 \exp\left(-0.908 \sqrt{\frac{Dt}{Rh}}\right) + 0.509 \exp\left(-1.679 \frac{Dt}{Rh}\right) \quad \text{Eq. 2}$$

$$\frac{F_0}{F_\infty} = 2(1 - v_s) \quad \text{Eq. 3}$$

$$\xi_p = 2 \left( \frac{\eta}{2} \frac{D(1 - 2v_s)}{G(1 - v_s)} \right)^{\frac{1}{2}} \quad \text{Eq. 4}$$

Methods and Materials

SWNT Sensor and Gel Platform Fabrication

SWNT were suspended in chitosan according to Reuel, N. F. et al. *J. Am. Chem. Soc.* 133, 17923-17933 (2011), which is incorporated by reference in its entirety. In brief, 3 mg of purified HiPCO SWNT (Unidym) were added to 20 ml of chistosan suspension (0.25 wt % in water containing 1 vol % acetic acid—Sigma). The resulting mixture was tip sonicated (¼" tip Cole Parmer, Model CV18) at 10 W for 45 minutes in an ice bath and table-top centrifuged three times at 13.2 RPM for 90 min each, while collecting the suspended SWNT supernatant and discarding the aggregate pellet after each cycle. The SWNT was then mixed at a 50:50 volume ratio with the polyacrylamide mixture for casting as the top layer. The amount of monomer (acrylamide) and cross-linker (N,N'-Methylenebisacrylamide—both Sigma) are specified using standard % T % C nomenclature, where % T refers to the overall weight % of polymer (monomer and crosslinker) in the solution and % C refers to the wt % of the total polymer that is cross linker Surface gels with a 3% C and 1% T composition performed well. A substrate gel (6% T, 1% C) was also prepared. TEMED (Tetramethylethylenediamine) was added in at 0.7 vol % in both the top and bottom gel solutions to stabilize the radical reaction. A fresh initiator solution of 1 wt % Ammonium persulfate (APS) was made immediately prior to each gel batch. The APS, bottom and top gel solutions, and substrate chips (8 chamber Lab-Tek by Nunc) were degassed in the glove box antechamber to remove absorbed and dissolved oxygen. Within a nitrogen controlled glove box (MBraun LABstar), 1 vol % of the APS solution was added to the substrate gel to initiate the polymerization and it was immediately cast (100 ul to each well) and then allowed to cure for one hour. The top gel was then initiated with 1 vol % APS and immediately spotted at 20 ul to each gel surface and allowed to cure for 1 hour.

The functionalization steps of the chitosan wrapped SWNT is also similar to that described in Reuel, N. F. et al. *J. Am. Chem. Soc.* 133, 17923-17933 (2011), which is incorporated by reference in its entirety. In brief, the amine groups of the chitosan were reacted with succinic anhydride (133 mM in PBS 7.4 buffer—Sigma) overnight and then washed thoroughly with water. The carboxylic acid functional groups were then activated with 100 mM EDC and 520 mM NHS (Sigma) in MES Buffer pH 4.7 (Pierce) for 2 hours. After washing with water thoroughly, the gels were then reacted with 34 mM Nα,Nα-Bis(carboxymethyl)-L-lysine hydrate (Sigma) in PBS 7.4 buffer overnight. The gels were then washed an incubated with a 100 mM nickel sulfate solution for 20 minutes. These chips were then washed thoroughly in water and stored in water.

Poroelastic Relaxation Indentation and Dextran Release Curves

The gel pore size was first evaluated by poroelastic indentation by AFM as explained in the Kalcioglu, Z. I., et al. *Soft Matter* 8, 3393-3398 (2012), which is incorporated by reference in its entirety. In brief, a short silicon tip with a 45 μm polystyrene sphere (Novascan) was fitted on an AFM (Asylum Research—MFP3D) and the IgorPro software indentation panel was used to drive the tip into the gel at a specified distance and record the force over time. This was done in replicates for multiple sites on each gel type. A custom Matlab algorithm was then used to analyze the force relaxation curves and determine the average pore size.

FITC-conjugated dextran particles (Invitrogen) of various sizes (10, 40, 70, and 500 kD) were also absorbed into 150 μl cylindrical gel plugs over 48 hours. The impregnated gels were then removed, washed, and inserted into clean water. The release of the FITC particles was observed by sampling the exterior fluid and assaying the FITC content with a plate reader. Using standard curves, the release was then determined in terms of cumulative mass release over time.

Data Collection on nIR Inverted Microscope

SWNT sensor data was collected on a custom inverted microscope (Zeiss D.1 Observer) that was fitted with a 660 nm laser (Crystal Laser, 100 mW). A 20× planar objective (Zeiss) was used and the emission intensities were recorded by a nitrogen-cooled InGaAs array (Princeton Instruments). Win Spec software (Princeton Instruments) was used to collect the SWNT emission and saved as an image stack TIF file. This file was then analyzed using Matlab. Analyte samples were added to the sensor gels by hand, applying the 100 μl sample to the lower right corner of the well, so as not to place the plastic pipette tip in the laser beam path.

To prepare a sensor gel for testing, it was first thoroughly washed with PBS to exchange the buffer and then allowed to incubate with the his-tag sensor protein (Protein A (Abcam) or PSA lectin (Vector Labs)) at 500 μg/ml overnight. The gel was again washed thoroughly with PBS and then fitted on the microscope for testing.

HEK Cell Line Generation and CHO Origin

A tricistronic expression cassette pLB2-CMV-GFP-TA99 was created using 2A skip peptides (see Hu, T., et al. *Biotechnology Letters* 31, 353-359 (2009), which is incorporated by reference in its entirety). The light and heavy chain sequences of TA99, a murine IgG2a antibody (Thomson, T. M., et al. *J. of Investigative Dermatology* 85, 169-174 (1985), which is incorporated by reference in its entirety), were linked by a T2A sequence. The expression cassette was cloned into the lentiviral vector, pLB2 (Stern, P. et al. *PNAS* 105, 13895-13900 (2008), which is incorporated by reference in its entirety), modified with a CMV promoter driving GFP-F2A expression, creating the complete plasmid sequence of pLB2-CMV-GFP-F2A-LC-T2A-HC. All cloning was performed using overlap extension PCR. HEK- GFP-TA99 cells were generated using a modified version of a previously described protocol (see Kuroda, H., et al. *J. of Virological Methods* 157, 113-121 (2009), which is incorporated by reference in its entirety). Briefly, HEK-293FT cells (Invitrogen) were transfected with the following plasmids: pLB2-CMV-GFP-TA99, pCMV-dR8.91, and pCMV-VSV-G at a mass ratio of 2:1:1 using PEI (see Zufferey, R., et al. *Nature Biotechnology* 15, 871-875 (1997); and Dull, T. et al. *J. of Virology* 72, 8463-8471 (1998), each of which is incorporated by reference in its entirety). After 24 hours, fresh media was exchanged. 48 and 72 hours later, supernatant containing lentiviral particles was harvested. HEK-293 cells were transduced twice for 24 hours by incubation with freshly harvested supernatant supplemented with protamine sulfate at 5 µg/mL. GFP positive cells were selected to a purity of greater than 95% using flow fluorescence activated cell sorting.

Details on the generation of the CHO cell line can be found in Hezareh, M., et al. *J. Virology* 75, 12161-12168 (2001), which is incorporated by reference in its entirety.

Cell Passaging and Culture

For standard culture the medias used were DMEM (with 4.5 g/L glucose, 10% heat inactivated FBS (Invitrogen), 2 mM L-glutamine, 100 U/ml Penicillin, 100 U/ml Streptomycin—rest Sigma), and GMEM (same additives—Sigma) for the HEK and CHO cultures, respectively. For cultures used in experiments, a serum free media was used for growth and as a buffer in the sensor gel (Invitrogen Freestyle 293). To passage the cells, they were allowed to grow to confluence, washed with PBS, and then released with Trypsin (0.05% w/0.53 mM EDTA). The cells were then pelleted, resuspended in fresh media and diluted at a 1:5 ratio. The cells were passaged every 2-3 days and discarded after the 20$^{th}$ passage.

Hypermannosylation CHO Culture Experiment

CHO cells were seeded at equal density in small culture flasks (25 cm$^2$—Sarstedt) and allowed to grow to confluence with regular GMEM media (overnight). The growth media was then exchanged with 3 ml serum free media (Freestlye 293 Invitrogen) and the cells were allowed to produce for 24 hours. The media was then saved and a fresh 3 ml of serum-free media was added for the next 24 cycle. This was repeated for 10 days. The IgG content was measured by ELISA (ICL Lab, Inc.) and the samples were diluted to 10 ng/ml in Freestyle to run on the PSA-incubated SWNT gels.

Other embodiments are within the scope of the following claims.

What is claimed is:

1. A sensor for detecting an analyte, comprising:
a support and
a multilayer configuration comprising:
   a substrate hydrogel arranged on the support, the substrate hydrogel composed of materials that are substantially free of background photoluminescence such that the substrate hydrogel shifts focal volume off the support;
   a sensor hydrogel arranged as a capping layer on the substrate hydrogel such that the substrate hydrogel is an intermediate layer that separates the sensor from the support, such that the focal plane does not include any portion of the support, and the capping layer having larger pore sizes than the substrate hydrogel to allow antibodies to diffuse to sensor sites;
   a photoluminescent nanostructure dispersed in the sensor hydrogel, but not in the substrate hydrogel;
   an analyte; and
   an analyte-binding compound associated with the photoluminescent nanostructure the presence of the analyte altering the photoluminescent properties of the photoluminescent nanostructure.

2. The sensor of claim 1, further comprising a linker, wherein the analyte-binding compound is associated with the photoluminescent nanostructure via the linker.

3. The sensor of claim 2, wherein the linker is associated with the nanostructure by a non-covalent interaction.

4. The sensor of claim 2, wherein the linker includes a polymer.

5. The sensor of claim 4, wherein the polymer includes a polypeptide, a polynucleotide or a polysaccharide.

6. The sensor of claim 5, wherein the polysaccharide is chitosan.

7. The sensor of claim 4, wherein the polymer is cross-linked, thereby providing clusters of photoluminescent nanostructures.

8. The sensor of claim 2, wherein the linker further includes a first binding partner, and the analyte-binding protein includes a second binding partner, selected such that the first binding partner and second binding partner bind together.

9. The sensor of claim 8, wherein the first binding partner includes a metal ion.

10. The sensor of claim 9, wherein the linker further includes a chelating region.

11. The sensor of claim 1, wherein the analyte-binding compound is an analyte-binding protein.

12. The sensor of claim 1, wherein the substrate hydrogel includes poly(acrylamide).

13. The sensor of claim 1 wherein the sensor hydrogel includes poly(acrylamide).

14. A method of making a sensor for detecting an analyte, comprising:
arranging a multilayer configuration including a substrate hydrogel on a support, the substrate hydrogel composed of materials that are substantially free of background photoluminescence such that the substrate hydrogel shifts focal volume off the support;
casting a sensor hydrogel from a sensor hydrogel precursor composition on the substrate hydrogel as a capping layer such that the substrate hydrogel is an intermediate layer, the sensor hydrogel separated from the support by the substrate hydrogel, and the capping layer having larger pore sizes than the substrate hydrogel to allow antibodies to diffuse to sensor sites,
wherein the sensor hydrogel precursor composition includes a photoluminescent nanostructure in the sensor hydrogel, but not in the substrate hydrogel; and an analyte-binding compound associated with the photoluminescent nanostructure, the presence of the analyte altering the photoluminescent properties of the photoluminescent nanostructure.

15. The method of claim 14, wherein arranging the substrate hydrogel on the support includes casting the substrate hydrogel from a substrate hydrogel precursor composition on the support.

16. The method of claim 14, wherein the substrate hydrogel includes poly(acrylamide).

17. The method of claim 14, wherein the sensor hydrogel includes poly(acrylamide).

18. A method of detecting an analyte, comprising:
contacting a composition including an analyte to a multilayer sensor including:
a support
a substrate hydrogel arranged on the support, the substrate hydrogel designed to shift focal volume off the support;

a sensor hydrogel arranged as a capping layer on the substrate hydrogel such that the substrate hydrogel is an intermediate layer that separates the sensor from the support, and such that the focal plane does not include any portion of the support, and the capping layer having larger pore sizes than the substrate hydrogel to allow antibodies to diffuse to sensor sites;

a photoluminescent nanostructure dispersed in the sensor hydrogel, but not in the substrate hydrogel;

an analyte; and an analyte-binding compound associated with the photoluminescent nanostructure; and detecting an emission from the photoluminescent nanostructure the presence of the analyte altering the photoluminescent properties of the photoluminescent nanostructure.

19. The method of claim 18, further comprising detecting photoluminescence from the photoluminescent nanostructure.

20. The method of claim 19, where detecting photoluminescence includes focusing an objective on the sensor hydrogel.

\* \* \* \* \*